United States Patent
Wolf et al.

(10) Patent No.: US 12,374,430 B2
(45) Date of Patent: *Jul. 29, 2025

(54) SYSTEMS AND METHODS FOR ASSOCIATING COMPOUNDS WITH PROPERTIES USING CLIQUE ANALYSIS OF CELL-BASED DATA

(71) Applicant: Flagship Pioneering Innovations VI, LLC, Cambridge, MA (US)

(72) Inventors: Fabian Alexander Wolf, Munich (DE); Umut Eser, Cambridge, MA (US); Nicholas McCartney Plugis, Cambridge, MA (US)

(73) Assignee: FLAGSHIP PIONEERING INNOVATIONS VI, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/617,486

(22) Filed: Mar. 26, 2024

(65) Prior Publication Data
US 2024/0242786 A1 Jul. 18, 2024

Related U.S. Application Data

(63) Continuation of application No. 17/841,536, filed on Jun. 15, 2022, now Pat. No. 11,978,538.

(60) Provisional application No. 63/210,736, filed on Jun. 15, 2021.

(51) Int. Cl.
*G01N 33/48* (2006.01)
*G16C 20/30* (2019.01)

(52) U.S. Cl.
CPC .................................. *G16C 20/30* (2019.02)

(58) Field of Classification Search
None
See application file for complete search history.

(56) References Cited

U.S. PATENT DOCUMENTS

2018/0371408 A1 12/2018 Yu
2023/0204569 A1 6/2023 Herz

OTHER PUBLICATIONS

Bero, S. A., et al., "Weighted Tanimoto Coefficient for 3D Molecule Structure Similarity Measurement," arXiv:1806.05237, Jun. 10, 2018.
Beske, Oren E., and Simon Goldbard. "High-throughput cell analysis using multiplexed array technologies." Drug Discovery Today 7.18 (2002): S131-S135.
Carpenter, A.E., et al., "CellProfiler: image analysis software for identifying and quantifyingcell phenotypes," Genome Biology 2006, 7:R100.
Davis, J. et al., "L1000 SOP," Connectivity Map, published by the Broad Institute, Dec. 20, 2016.
Duran-Frigola, M. et al., "Extending the small-molecule similarity principle to all levels of biology with the Chemical Checker", Nature Biotechnology, v. 38, No. 9, p. 1087-1096 (May 18, 2020).
Ekwall, Bjorn. "Screening of toxic compounds in mammalian cell cultures." Annals of the New York Academy of Sciences 407 (1983): 64-77.
Gustafsdottir, S.M., et al., "Multiplex Cytological Profiling Assay to Measure Diverse Cellular States," PLOS One, Dec. 2013, vol. 8, Issue 12.
Lopez-Paz, D., et al., "The Randomized Dependence Coefficient," arXiv:1304.7717v2 [ stat.ML] Jun. 3, 2013.
Monks, Anne, et al. "Feasibility of a high-flux anticancer drug screen using a diverse panel of cultured human tumor cell lines." JNCI: Journal of the National Cancer Institute 83.11 (1991): 757-766.
Newgard, C.B., et al., "A Branched-Chain Amino Acid-Related Metabolic Signature that Differentiates Obese and Lean Humans and Contributes to Insulin Resistance," Cell Metab. Apr. 2009; 9(4): 311-326.
Quigley, I.K. et al., "Rfx2 Stabilizes Foxj1 Binding at Chromatin Loops to Enable Multiciliated Cell Gene Expression," PLOS Genetics | DOI:10.1371/journal.pgen.1006538 Jan. 19, 2017.
Rodgers, J.L., et al., "Thirteen Ways to Look at the Correlation Coefficient," The American Statistician, vol. 42, No. 1. (Feb. 1988), pp. 59-66.
Scheiber, Josef, et al. "Mapping adverse drug reactions in chemical space." Journal of medicinal chemistry 52. 9 (2009): 3103-3107.
Subramanian, A., et al., "A Next Generation Connectivity Map: L1000 Platform and the First 1,000,000 Profiles," Cell 171, 1437-1452, Nov. 30, 2017.
Székely, G., et al., "Measuring and Testing Dependence by Correlation of Distances," The Annals of Statistics, 2007, vol. 35, No. 6, 2769-2794.
Wang, T.J., et al., "Metabolite Profiles and the Risk of Developing Diabetes," Nat Med. Apr. 2011; 17(4): 448-453.
Zaraitsky, A., et al., "Interpretable deep learning of label-free live cell images uncovers functional hallmarks of highly-metastatic melanoma," https://doi.org/10.1101/2020.05.15.096628.
Zhang, Bijun, et al. "Design of chemical space networks using a Tanimoto similarity variant based upon maximum common substructures." Journal of computer-aided molecular design 29.10 (2015): 937-950.

*Primary Examiner* — Anna Skibinsky

(57) ABSTRACT

Methods of associating a test compound with a compound property. One or more datasets including: for each of a plurality of cell lines and each of a plurality of compounds: for each respective exposure condition: a corresponding response signature for the respective compound in the respective cell line under the respective exposure condition is obtained. A correlation is determined for each unique combination of exposure conditions for a respective pair of compounds based on the corresponding response signature. A weight is determined for each respective pair of compounds based on the determined correlations. A plurality of compound clusters is formed, where each cluster represents compounds that satisfy one or more weight criteria with respect to a particular compound. A compound property of the test compound is determined from properties of one or more compounds in a one or more compound clusters that contain the test compound.

29 Claims, 17 Drawing Sheets

Non-Persistent Memory 111

| | |
|---|---|
| Statistics data store | 150 |
| Compound 1 vs Compound 2 | 152-(1-2) |
|   Correlations | 153-(1-2) |
|     Cell line 1 | 154-(1-2)-1 |
|       Condition 1-1-1 vs condition 2-1-1 correlation | 156-(1-2)-1-(1-1) |
|       Condition 1-1-1 vs condition 2-1-2 correlation | 156-(1-2)-1-(1-2) |
|       ⋮ | |
|       Condition 1-1-1 vs condition 2-1-H correlation | 156-(1-2)-1-(1-H) |
|       ⋮ | |
|       Condition 1-1-E vs condition 2-1-H correlation | 156-(1-2)-1-(E-H) |
|     Cell line 2 | 154-(1-2)-2 |
|       Condition 1-2-1 vs condition 2-2-1 correlation | 156-(1-2)-2-(1-1) |
|       Condition 1-2-1 vs condition 2-2-2 correlation | 156-(1-2)-2-(1-2) |
|       ⋮ | |
|       Condition 1-2-F vs condition 2-2-I correlation | 156-(1-2)-2-(F-I) |
|     ⋮ | |
|     Cell line A(1-2) | 154-(1-2)-A(1-2) |
|       Condition 1-A(1-2)-1 vs condition 2-A(1-2)-1 corr. | 156-(1-2)-A(1-2)-(1-1) |
|       Condition 1-A(1-2)-1 vs condition 2-A(1-2)-2 corr. | 156-(1-2)-A(1-2)-(1-2) |
|       ⋮ | |
|       Condition 1-A(1-2)-J vs condition 2-A(1-2)-K corr. | 156-(1-2)-A(1-2)-(J-K) |
|   Weights | 160-(1-2) |
|   Comparison score | 168-(1-2) |
| Compound 1 vs Compound 3 | 152-(1-3) |
|   Correlations | 153-(1-3) |
|   Weights | 160-(1-3) |
|   Comparison score | 168-(1-3) |
|   ⋮ | |
| Compound 1 vs Compound B | 152-(1-B) |
| Compound 2 vs Compound 1 | 152-(2-1) |
| ⋮ | |
| Compound B vs Compound B-1 | 152-(B-(B-1)) |

302 Obtain one or more datasets in electronic form, the one or more datasets including or collectively including: for each respective cell line in a plurality of cell lines, where the plurality of cell lines includes five or more cell lines: for each respective compound in a plurality of compounds: for each respective exposure condition in one or more exposure conditions for the respective compound: a corresponding response signature for the respective compound in the respective cell line under the respective exposure condition, the corresponding response signature including a corresponding plurality of quantitative biomarker measurements of the respective cell line across a plurality of biomarkers upon exposure of the respective cell line to the respective compound at the respective exposure condition, where the plurality of biomarkers includes one hundred or more biomarkers.

304 Each corresponding response signature is normalized against a response signature of one or more control genes in the respective cell line.

306 The plurality of cell lines includes 6, 7, 8, 9, 10, 11, 12, 13, 14, 15, 16, 17, 18, 19, 20, 21, 22, 23, 24, 25, or more than 25 cell lines.

308 The plurality of compounds is between 10 and $1 \times 10^8$ compounds, between 100 and $1 \times 10^7$ compounds, between 1000 and $1 \times 10^6$ compounds, or between 10,000 and 100,000 compounds.

310 The respective exposure condition is a duration of exposure, a concentration of the respective compound, an environmental condition of the exposure, or a combination thereof.

312 The plurality of biomarkers are nucleic acids, ribonucleic acids, carbohydrates, lipids, epigenetic features, metabolites, proteins, cell morphological features, or a combination thereof.

314 Each quantitative biomarker measurement in the corresponding plurality of quantitative biomarker measurement is a colorimetric measurement, a fluorescence measurement, a luminescence measurement, or a resonance energy transfer (FRET) measurement.

FIG. 3A

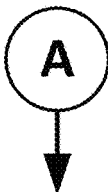

316 For each respective cell line in the plurality of cell lines, for each respective pair of compounds in the plurality of compounds:

318 Determine, for each unique combination of respective exposure conditions for the respective pair of compounds, a corresponding correlation of the corresponding plurality of quantitative biomarker measurements for the respective pair of compounds across the plurality of biomarkers, thereby determining a plurality of correlation values for the respective pair of compounds.

322 The corresponding correlation of the corresponding plurality of quantitative biomarker measurements for the respective pair of compounds across the plurality of biomarkers is a Pearson correlation.

324 Determine one or more weights for the respective pair of compounds from the one or more correlations values for the respective pair of compounds.

320 For a respective pair of compounds in the plurality of compounds, the one or more weights for the respective pair of compounds includes a plurality of weights, each respective weight in the plurality of weights corresponding to a comparison between (i) a respective response signature corresponding to exposure of a first respective compound in the respective pair of compounds to a respective cell line in the plurality of cell lines under a respective exposure condition in the plurality of exposure conditions, and (ii) each respective response signature corresponding to exposure of the second respective compound in the respective pair of compounds to the respective cell line under a respective exposure condition in the plurality of exposure conditions

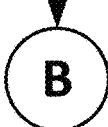

FIG. 3B

326 Form a plurality of compound clusters, each respective compound cluster representing a first respective compound in the plurality of compounds and including a corresponding subset of compounds in the plurality of compounds, where each respective compound in the corresponding subset of compounds satisfies one or more weight criteria with respect to the first respective compound.

328 The one or more weight criteria includes a requirement that the respective pair of compounds in the corresponding unique subset of compounds have a correlation value across all or a subset of the plurality of cell lines that is within a threshold percent of an upper correlation bound identified for the plurality of compounds across the plurality of cell lines.

330 The threshold percent is between five percent and fifty percent (e.g., five, ten, fifteen, twenty, twenty-five, thirty, thirty-five, forty, forty-five, or fifty percent).

332 The one or more weight criteria is a plurality of weight criterion and the plurality of weight criteria further includes a requirement that the subset of the plurality of cells lines be at least five different cell lines.

334 The one or more weight criteria is a plurality of weight criterion and the plurality of weight criteria further includes a requirement that the subset of the plurality of cells lines be at least 3, 4, 5, 6, 7, 8, 9, 10, 11, 12, 13, 14, 15, 16, 17, 18, 19, or 20 different cell lines.

336 One or more compound clusters in the plurality of compound clusters that contain the test compound for test compound is a drug for a first disease indication, and the method further includes using the identifying the compound property of test compound from one or more properties of one or more compounds in one or more compound clusters in the plurality of compound clusters to repurpose the drug for a second disease indication.

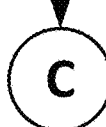

FIG. 3C

SYSTEMS AND METHODS FOR ASSOCIATING COMPOUNDS WITH PROPERTIES USING CLIQUE ANALYSIS OF CELL-BASED DATA

CROSS REFERENCE TO RELATED APPLICATIONS

This application is a continuation of U.S. patent application Ser. No. 17/841,536, entitled "SYSTEMS AND METHODS FOR ASSOCIATING COMPOUNDS WITH PROPERTIES USING CLIQUE ANALYSIS OF CELL-BASED DATA," filed Jun. 15, 2022, which claims priority to U.S. Provisional Patent Application No. 63/210,736, entitled "SYSTEMS AND METHODS FOR ASSOCIATING COMPOUNDS WITH PROPERTIES USING CLIQUE ANALYSIS OF CELL-BASED DATA," filed Jun. 15, 2021.

TECHNICAL FIELD

The present disclosure relates generally to systems and methods for analyzing similarities among perturbagens. More particularly, the present invention relates to predicting the behavior of a perturbagen based on similarities with other perturbagens across a range of cell lines.

BACKGROUND

The study of cellular mechanisms is important for understanding disease. However, tissues are complex ecosystems of individual cells, where dysregulation of cell state is the basis of disease. Existing drug discovery efforts seek to characterize the molecular mechanisms that cause cells to transition from healthy to disease states, and to identify pharmacological approaches to reverse or inhibit these transitions. Past efforts have also sought to identify molecular signatures characterizing these transitions, and to identify pharmacological approaches that reverse these signatures.

Phenotypical characterization of perturbagens is crucial for rational drug discovery and/or rational drug design. Conventionally, phenotypic characterization of perturbagens includes evaluating the transcriptional response in a cell line upon exposure of the cell line to the perturbagen. However, characterizing a perturbagen with the transcriptional response it causes in a single cell line and/or under a single exposure condition is inefficient, as the perturbagen can cause different transcriptional responses in different cell types and under different exposure conditions. This reflects the fact that a particular transcriptional response is caused by a combination of the cellular programming of the particular cell line and the environmental conditions under which the cell line is cultured, in addition to the specific effects of the perturbagen. This creates a context-dependency problem for the interpretation of response signatures, as they carry the signatures of both the cell type and the perturbation, under the given environmental condition. Therefore, inferring the effect of a perturbagen in one cell type by evaluating its effect on other cell types leads to poor performance.

SUMMARY

Given the above background, what is needed in the art are improved systems and methods for rational drug discovery and drug design that better model the effects of a perturbagen independent of a particular cell context. The present disclosure addresses these, as well as other, needs in the field of pharmaceutical discovery and design.

In some embodiments, the systems and methods described herein correlate phenotypic responses to perturbagen challenge to the phenotypic responses caused by other perturbagens across different cell types. In this fashion, perturbagens that effect highly correlated responses across a range of cell lines are grouped into a compound cluster. Such compound clusters provide several advantages and enable valuable downstream applications. For example, the compound clustering methods described herein is more resilient to batch effects and technological/platform biases, as it only requires the internal structure of the experiments, which is already conditioned on the system of measurement. Second, the compound clustering methodologies described herein provide mechanistic insights that can be propagated from well-studied/known perturbagens to unknown/uncharacterized perturbagens identified in one or more of the same compound clusters. Third, identification of structural analogs in a compound cluster enable Structure-Activity Relationship (SAR) analysis which can be generalized to Structure-Behavior Relationship Analysis, facilitating rational design of new chemical entities with desired properties. Finally, knowledge of the molecular targets of some perturbagens within a compound cluster facilitates identification of dynamic causal subnetworks that drive cellular behavior changes.

In one aspect, the disclosure provides a method of associating a test compound with a compound property, where the test compound is in a plurality of compounds. The method includes obtaining one or more datasets in electronic form, the one or more datasets including or collectively including: for each respective cell line in a plurality of cell lines, where the plurality of cell lines includes five or more cell lines: for each respective compound in a plurality of compounds: for each respective exposure condition in one or more exposure conditions for the respective compound: a corresponding response signature for the respective compound in the respective cell line under the respective exposure condition, the corresponding response signature including a corresponding plurality of quantitative biomarker measurements of the respective cell line across a plurality of biomarkers upon exposure of the respective cell line to the respective compound at the respective exposure condition, where the plurality of biomarkers includes one hundred or more biomarkers.

For each respective cell line in the plurality of cell lines, for each respective pair of compounds in the plurality of compounds, the method includes determining, for each unique combination of respective exposure conditions for the respective pair of compounds, a corresponding correlation of the corresponding plurality of quantitative biomarker measurements for the respective pair of compounds across the plurality of biomarkers, thereby determining one or more correlation values for the respective pair of compounds. For each respective pair of compounds in the plurality of compounds, the method also includes determining one or more weights for the respective pair of compounds from the one or more correlations values for the respective pair of compounds.

The method also includes forming a plurality of compound clusters, each respective compound cluster representing a respective compound in the plurality of compounds and including a corresponding subset of compounds in the plurality of compounds, where each respective compound in the corresponding subset of compounds satisfies one or more weight criteria with respect to respective compound.

The method also includes identifying the compound property of the test compound from one or more properties of one or more compounds in one or more compound clusters in the plurality of compound clusters that contain the test compound.

Another aspect of the present disclosure provides a method of associating a test compound with a compound property. The test compound is in a plurality of compounds. The method comprises (e.g., at a computer system comprising a memory and one or more processors) (A) obtaining one or more datasets in electronic form. The one or more datasets comprising or collectively comprise, for each respective cell line in a plurality of cell lines, where the plurality of cell lines comprises five or more cell lines, for each respective compound in the plurality of compounds, for each respective exposure condition in a plurality of exposure conditions for the respective compound: a corresponding response signature for the respective compound in the respective cell line under the respective exposure condition. This corresponding response signature comprises a corresponding plurality of quantitative biomarker measurements of the respective cell line across a plurality of biomarkers upon exposure of the respective cell line to the respective compound at the respective exposure condition. In some embodiments, the plurality of biomarkers comprises 10, 20, 50, or one hundred or more biomarkers.

The method further comprises (B) for each respective cell line in the plurality of cell lines, for each respective pair of compounds in the plurality of compounds: (i) determining, for each unique combination of respective exposure conditions for the respective pair of compounds, a corresponding correlation of the corresponding plurality of quantitative biomarker measurements for the respective pair of compounds across the plurality of biomarkers, thereby determining one or more correlation values for the respective pair of compounds, and (ii) determining one or more weights for the respective pair of compounds from the one or more correlations values for the respective pair of compounds.

The method further comprises (C) forming a plurality of compound clusters. Each respective compound cluster represents a different compound in the plurality of compounds and comprises a corresponding subset of compounds in the plurality of compounds. Each respective compound in the corresponding subset of compounds satisfies one or more weight criteria with respect to the different compound.

The method further comprises (D) identifying the compound property of the test compound from one or more properties of one or more compounds in one or more compound clusters in the plurality of compound clusters that contain the test compound.

In some embodiments, the one or more weight criteria comprises a requirement that the respective pair of compounds in the corresponding unique subset of compounds have a correlation value across all or a subset of the plurality of cell lines that is within a threshold percent of an upper correlation bound identified for the plurality of compounds across the plurality of cell lines. In some such embodiments, the one or more weight criteria is a plurality of weight criteria and the plurality of weight criteria further comprises a requirement that the subset of the plurality of cells lines be at least five different cell lines. In some such embodiments, the one or more weight criteria is a plurality of weight criteria and the plurality of weight criteria further comprises a requirement that the subset of the plurality of cells lines be at least 3, 4, 5, 6, 7, 8, 9, 10, 11, 12, 13, 14, 15, 16, 17, 18, 19, 20, 30, 40, 50, 60, or 100 different cell lines.

In some embodiments, the threshold percent is between five percent and fifty percent. In some embodiments, the threshold percent is five, ten, fifteen, twenty, twenty-five, thirty, thirty-five, forty, forty-five, or fifty percent.

In some embodiments, each corresponding response signature is normalized against a response signature of one or more control genes in the respective cell line.

In some embodiments, the plurality of cell lines comprises 3, 4, 5, 6, 7, 8, 9, 10, 11, 12, 13, 14, 15, 16, 17, 18, 19, 20, 30, 40, 50, 60, or 100 different cell lines.

In some embodiments, the plurality of compounds is between 10 and $1\times10^8$ compounds, between 100 and $1\times10^7$ compounds, between 1000 and $1\times10^6$ compounds, or between 10,000 and 100,000 compounds.

In some embodiments, the respective exposure condition is a duration of exposure, a concentration of the respective compound, an environmental condition of the exposure, or a combination thereof.

In some embodiments, for a respective pair of compounds in the plurality of compounds, the one or more weights for the respective pair of compounds comprises a plurality of weights. In such some embodiments, each respective weight in the plurality of weights corresponds to a comparison between (i) a respective response signature corresponding to exposure of a first respective compound in the respective pair of compounds to a respective cell line in the plurality of cell lines under a respective exposure condition in the plurality of exposure conditions, and (ii) each respective response signature corresponding to exposure of the second respective compound in the respective pair of compounds to the respective cell line under a respective exposure condition in the plurality of exposure conditions. In some such embodiments, for a respective weight in the plurality of weights, the weight is determined by taking a measure of central tendency of the corresponding plurality of correlation values determined for the respective pair of compounds.

In some embodiments, the corresponding correlation of the corresponding plurality of quantitative biomarker measurements for the respective pair of compounds across the plurality of biomarkers is a Pearson correlation.

In some embodiments, one or more compound clusters in the plurality of compound clusters that contain the test compound include a drug for a first disease indication, and the method further comprises using the identifying the compound property of test compound from one or more properties of one or more compounds in one or more compound clusters in the plurality of compound clusters to repurpose the drug for a second disease indication.

In some embodiments, the compound property of the test compound is determined from one or more properties of one or more compounds in the compound cluster in the plurality of compound clusters associated with the test compound though pharmacophore analysis.

In some embodiments, the compound property of the test compound is a mechanism-of-action annotation.

In some embodiments, the plurality of biomarkers are nucleic acids, ribonucleic acids, carbohydrates, lipids, epigenetic features, metabolites, proteins, cell morphological features, or a combination thereof.

In some embodiments, the method further comprises using the compound property of the test compound and the one or more properties of the one or more compounds in the one or more compound clusters in the plurality of compound clusters that contain the test compound to identify a molecular target for a disease indication.

In some embodiments, each quantitative biomarker measurement in the corresponding plurality of quantitative biomarker measurement is a colorimetric measurement, a fluorescence measurement, a luminescence measurement, or a resonance energy transfer (FRET) measurement.

In some embodiments, the forming (C) comprises, for each respective compound cluster in the plurality of compound clusters: determining, for each respective pair of compounds in a respective subset of the plurality of pairs compounds that comprises the corresponding compound represented by the respective compound cluster, a corresponding correlation score from the plurality of weights for the respective pair of compounds, for each respective cell line in the plurality of cell lines; and identifying which respective pairs of compounds, in the respective subset of the plurality of compounds, have a corresponding correlation score that is within a threshold percent of the upper correlation score bound across the respective subset of the plurality of compounds. In some such embodiments, for each respective pair of compounds in the respective subset of the plurality of pairs compounds, the correlation score is determined by: selecting, from each plurality of weights for the respective pair of compounds determined for a respective cell line in the plurality of cell lines, a corresponding subset of the plurality of weights, where each respective weight in the corresponding subset of the plurality of weights satisfies one or more significance criteria, and determining the corresponding correlation score for the respective pair of compounds from the corresponding subset of the plurality of weights, for each respective cell line in the plurality of cell lines. In some such embodiments, the corresponding correlation score for the respective pair of compounds is a measure of central tendency of the respective weights in the corresponding subset of the plurality of weights for the respective pair of compounds across each respective cell line in the plurality of cell lines.

In some embodiments, the identifying the compound property of the test compound from one or more properties of one or more compounds in one or more compound clusters in the plurality of compound clusters that contain the test compound comprises determining that one or more compound clusters in the plurality of compound clusters that contain the test compound also includes a first compound associated with a physiological condition. In some such embodiments, the method further comprises confirming the test compound is also associated with the physiological condition. In some such embodiments, the physiological condition is a disease and where the first compound causes or prevents the disease. In some such embodiments, a Tanimoto coefficient between a fingerprint of the test compound and a fingerprint of the first compound is less than 0.80, less than 0.70, less than 0.60, less than 0.50, or less than 0.40. In some embodiments, a Tanimoto coefficient between a fingerprint of the test compound and a fingerprint of the first compound is less than a threshold value (e.g., where the threshold value is a predetermined value between 0.30 and 0.99). In some such embodiments, the fingerprint is a Daylight fingerprint, a SMILES Transformer fingerprint, a ECFP4 fingerprint, a RNNS2S fingerprint, or a GraphConv fingerprint.

In some embodiments the corresponding plurality of quantitative biomarker measurements are cell-based assay abundance values for the plurality of biomarkers using cells of the respective cell line. In some such embodiments, each biomarker in the plurality of biomarkers is a different gene in a plurality of genes. In some such embodiments, the plurality of biomarkers comprises 10 biomarkers, comprises 100 biomarkers, comprises 1000 biomarkers, comprises 2000 biomarkers, comprises 3000 biomarkers, or comprises 5000 biomarkers.

In some embodiments, each cell line in the plurality of cell lines is human. In some embodiments each cell line in the plurality of cell lines is mammalian. In some embodiments each cell line in the plurality of cell lines is Eukaryotic.

In some embodiments, a cell line in the plurality of cell lines is drawn from cells of an organ (e.g., in the form of a biopsy from the organ, etc.). In some embodiments, the organ is heart, liver, lung, muscle, brain, pancreas, spleen, kidney, small intestine, uterus, or bladder.

In some embodiments, a cell line in the plurality cell lines is drawn from a tissue. In some such embodiments, the tissue is bone, cartilage, joint, tracheae, spinal cord, cornea, eye, skin, or blood vessel.

In some embodiments, a cell line in the plurality of cell lines is drawn from a plurality of stem cells. In some such embodiments, the plurality of stem cells is a plurality of embryonic stem cells, a plurality of adult stem cells, or a plurality of induced pluripotent stem cells (iPSC).

In some embodiments, a cell line in the plurality of cell lines is drawn from a plurality of primary human cells. In some such embodiments, the plurality of primary human cells are a plurality of CD34+ cells, a plurality of CD34+ hematopoietic stems, a plurality of progenitor cells (HSPC), a plurality of T-cells, a plurality of mesenchymal stem cells (MSC), a plurality of airway basal stem cells, or a plurality of induced pluripotent stem cells.

In some embodiments, a cell line in the plurality of cell lines is drawn from cells in umbilical cord blood, in peripheral blood, or in bone marrow.

In some embodiments, a cell line in the plurality of cell lines is drawn from a solid tissue. In some such embodiments, the solid tissue is placenta, liver, heart, brain, kidney, or gastrointestinal tract.

In some embodiments, a cell line in the plurality of cell lines is drawn from a plurality of differentiated cells. In some such embodiments, the plurality of differentiated cells is a plurality of megakaryocytes, a plurality of osteoblasts, a plurality of chondrocytes, a plurality of adipocytes, a plurality of hepatocytes, a plurality of hepatic mesothelial cells, a plurality of biliary epithelial cells, a plurality of hepatic stellate cells, a plurality of hepatic sinusoid endothelial cells, a plurality of Kupffer cells, a plurality of pit cells, a plurality of vascular endothelial cells, a plurality of pancreatic duct epithelial cells, a plurality of pancreatic duct cells, a plurality of centroacinous cells, a plurality of acinar cells, a plurality of islets of Langerhans, a plurality of cardiac muscle cells, a plurality of fibroblasts, a plurality of keratinocytes, a plurality of smooth muscle cells, a plurality of type I alveolar epithelial cells, a plurality of type II alveolar epithelial cells, a plurality of Clara cells, a plurality of ciliated epithelial cells, a plurality of basal cells, a plurality of goblet cells, a plurality of neuroendocrine cells, a plurality of kultschitzky cells, a plurality of renal tubular epithelial cells, a plurality of urothelial cells, a plurality of columnar epithelial cells, a plurality of glomerular epithelial cells, a plurality of glomerular endothelial cells, a plurality of podocytes, a plurality of mesangium cells, a plurality of nerve cells, a plurality of astrocytes, a plurality of microglia, or a plurality of oligodendrocytes.

In some embodiments, the corresponding plurality of quantitative biomarker measurements are cell-based assay abundance values for the plurality of biomarkers from single-cell ribonucleic acid (RNA) sequencing (scRNA-seq) data of a plurality of cells of the respective cell line.

In some embodiments, the corresponding plurality of quantitative biomarker measurements are cell-based assay abundance values for the plurality of biomarkers from bulk ribonucleic acid (RNA) sequencing (scRNA-seq) data of a plurality of cells of the respective cell line.

In some embodiments, the corresponding plurality of quantitative biomarker measurements of the respective cell line comprises a quantitative measurement of an expression of particular gene, a particular mRNA associated with a gene, a carbohydrate, a lipid, an epigenetic feature, a metabolite, or a protein in the respective cell line.

In some embodiments, each respective biomarker in the plurality of biomarkers is a particular gene, a particular mRNA associated with a gene, a carbohydrate, a lipid, an epigenetic feature, a metabolite, a protein, or a combination thereof, and the corresponding quantitative biomarker measurement of the respective biomarker is determined by single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, or any combination thereof.

In some embodiments, the test compound is an organic compound having a molecular weight of less than 2000 Daltons.

In some embodiments, the test compound is an organic compound that satisfies each of the Lipinski rule of five criteria.

In some embodiments, the test compound is an organic compound that satisfies at least three criteria of the Lipinski rule of five criteria.

In some embodiments, the determining (B)(i) determines a corresponding correlation for each of five or more unique combinations of exposure conditions, for each of ten or more unique combinations of exposure conditions, for each of twenty or more unique combinations of exposure conditions, or for each of forty or more unique combinations of exposure conditions.

Another aspect of the present disclosure provides a method of associating a test compound with a compound property, where the test compound is in a plurality of compounds. The method comprises, at a computer system comprising a memory and one or more processors: (A) obtaining one or more dataset in electronic form, the one or more dataset comprising or collectively comprising: for each respective cell line in a plurality of cell lines, where the plurality of cell lines comprises five or more cell lines: for each respective compound in the plurality of compounds: for each respective exposure condition in one or more exposure conditions for the respective compound: a corresponding response signature for the respective compound in the respective cell line under the respective exposure condition. Here, the corresponding response signature comprises a corresponding plurality of quantitative biomarker measurements of the respective cell line across a plurality of biomarkers upon exposure of the respective cell line to the respective compound at the respective exposure condition. In some embodiments, the plurality of biomarkers comprises 10, 20, 30, 40, 50, 100, 200, 1000, 2000, or 4000 or more biomarkers. The method further comprises (B) for each respective cell line in the plurality of cell lines, for each respective pair of compounds in the plurality of compounds: (i) determining, for each unique combination of respective exposure conditions for the respective pair of compounds, a corresponding correlation of the corresponding plurality of quantitative biomarker measurements for the respective pair of compounds across the plurality of biomarkers, thereby determining a respective plurality of correlation values for the respective pair of compounds in the respective cell line, (ii) determining a respective plurality of weights for the respective pair of compounds in the respective cell line from the plurality of correlations values for the respective pair of compounds in the respective cell line, and (iii) identifying a corresponding subset of the respective plurality of weights for the respective pair of compounds in the respective cell line, where each respective weight in the corresponding subset of the plurality of weights satisfies one or more significance criteria. The method further comprises (C) determining, for each respective pair of compounds in the plurality of pairs of compounds, a corresponding comparison score from the respective subsets of the plurality of weights for the respective pair of compounds across the plurality of cell lines. The method further comprises (D) forming a plurality of compound clusters, each respective compound cluster in the plurality of compound clusters representing a respective compound in the plurality of compounds and comprising a corresponding subset of compounds in the plurality of compounds, where each respective compound in the corresponding subset of compounds satisfies one or more comparison score criteria with respect to the respective compound. The method further comprises (E) identifying the compound property of the test compound from one or more properties of one or more compounds in one or more compound clusters in the plurality of compound clusters that contain the test compound.

Another aspect of the present disclosure provides a computer system. The computer system comprises one or more processors and memory. The memory stores instructions for performing a method for associating a test compound with a compound property. The test compound is in a plurality of compounds. The method comprises (A) obtaining one or more datasets in electronic form, the one or more datasets comprising or collectively comprising: for each respective cell line in a plurality of cell lines, where the plurality of cell lines comprises five or more cell lines: for each respective compound in the plurality of compounds: for each respective exposure condition in a plurality of exposure conditions for the respective compound: a corresponding response signature for the respective compound in the respective cell line under the respective exposure condition. Here, the corresponding response signature comprising a corresponding plurality of quantitative biomarker measurements of the respective cell line across a plurality of biomarkers upon exposure of the respective cell line to the respective compound at the respective exposure condition. In some embodiments, the plurality of biomarkers comprises 10, 25, 100, 200, 500, 1000, or 2000 or more biomarkers. The method further comprises (B) for each respective cell line in the plurality of cell lines, for each respective pair of compounds in the plurality of compounds: (i) determining, for each unique combination of respective exposure conditions for the respective pair of compounds, a corresponding correlation of the corresponding plurality of quantitative biomarker measurements for the respective pair of compounds across the plurality of biomarkers, thereby determining one or more correlation values for the respective pair of compounds, and (ii) determining one or more weights for the respective pair of compounds from the one or more correlations values for the respective pair of compounds. The method further comprises (C) forming a plurality of compound clusters, each respective compound cluster representing a different compound in the plurality of compounds and comprising a corresponding subset of compounds in the plurality of compounds, where each respective compound in the corresponding subset of compounds satisfies one or more weight criteria with respect to the different compound. The method further comprises (D) identifying the compound property of the test compound from one or more properties of one or more compounds in one or more compound clusters in the plurality of compound clusters that contain the test compound.

Another aspect of the present disclosure provides a non-transitory computer-readable medium storing one or more computer programs, executable by a computer, for associating a test compound with a compound property. The test compound is in a plurality of compounds. The computer comprises one or more processors and a memory. The one or more computer programs collectively encode computer executable instructions that perform a method comprising: (A) obtaining one or more datasets in electronic form, the one or more datasets comprising or collectively comprising: for each respective cell line in a plurality of cell lines, where the plurality of cell lines comprises five or more cell lines: for each respective compound in the plurality of compounds: for each respective exposure condition in a plurality of exposure conditions for the respective compound: a corresponding response signature for the respective compound in the respective cell line under the respective exposure condition, the corresponding response signature comprising a corresponding plurality of quantitative biomarker measurements of the respective cell line across a plurality of biomarkers upon exposure of the respective cell line to the respective compound at the respective exposure condition. The plurality of biomarkers comprises 10, 25, 50, 100, 200, or 1000 or more biomarkers. The method further comprises (B) for each respective cell line in the plurality of cell lines, for each respective pair of compounds in the plurality of compounds: (i) determining, for each unique combination of respective exposure conditions for the respective pair of compounds, a corresponding correlation of the corresponding plurality of quantitative biomarker measurements for the respective pair of compounds across the plurality of biomarkers, thereby determining one or more correlation values for the respective pair of compounds, and (ii) determining one or more weights for the respective pair of compounds from the one or more correlations values for the respective pair of compounds. The method further comprises (C) forming a plurality of compound clusters, each respective compound cluster representing a different compound in the plurality of compounds and comprising a corresponding subset of compounds in the plurality of compounds, where each respective compound in the corresponding subset of compounds satisfies one or more weight criteria with respect to the different compound. The method further comprises (D) identifying the compound property of the test compound from one or more properties of one or more compounds in one or more compound clusters in the plurality of compound clusters that contain the test compound.

Yet other aspects of the present disclosure include computing systems for performing the methods described herein and non-transitory computer readable storage medium, where the non-transitory computer readable storage medium stores instructions, which when executed by a computer system, cause the computer system to perform any of the methods for analyzing cells described in the present disclosure.

BRIEF DESCRIPTION OF THE DRAWINGS

The embodiments disclosed herein are illustrated by way of example, and not by way of limitation, in the figures of the accompanying drawings. Like reference numerals refer to corresponding parts throughout the drawings.

FIGS. 1A, 1B, 1C, 1D, and 1E collectively illustrate a block diagram of an exemplary system and computing device for associating a test compound with a compound property, in accordance with various embodiments of the present disclosure;

FIGS. 3A, 3B, 3C, and 3D collectively provide a flow chart of processes and features of a system for associating a test compound with a compound property, in accordance with various embodiments of the present disclosure, where elements in dashed boxes are optional.

FIG. 7 shows mechanism of action annotation enrichment among perturbagens identified in the compound cluster.

FIG. 8 shows mechanism of action annotation enrichment among perturbagens identified in the compound cluster.

DETAILED DESCRIPTION

Introduction

Accurate phenotypical characterization of perturbagens is extremely important for accurate pharmaceutical discovery and rational drug design. There are several existing methods of characterizing perturbagens, including analysis of phenotypic responses in a cell line. However, none of them address the problem of context-dependency. For instance, any one transcriptional response is not necessarily a signature of a perturbagen. The response carries the signature of both the cell type and the perturbation. Therefore, inferring the effect of a perturbagen in a new cell type by looking at its effect on other cell types leads to poor performance.

Figure 4:
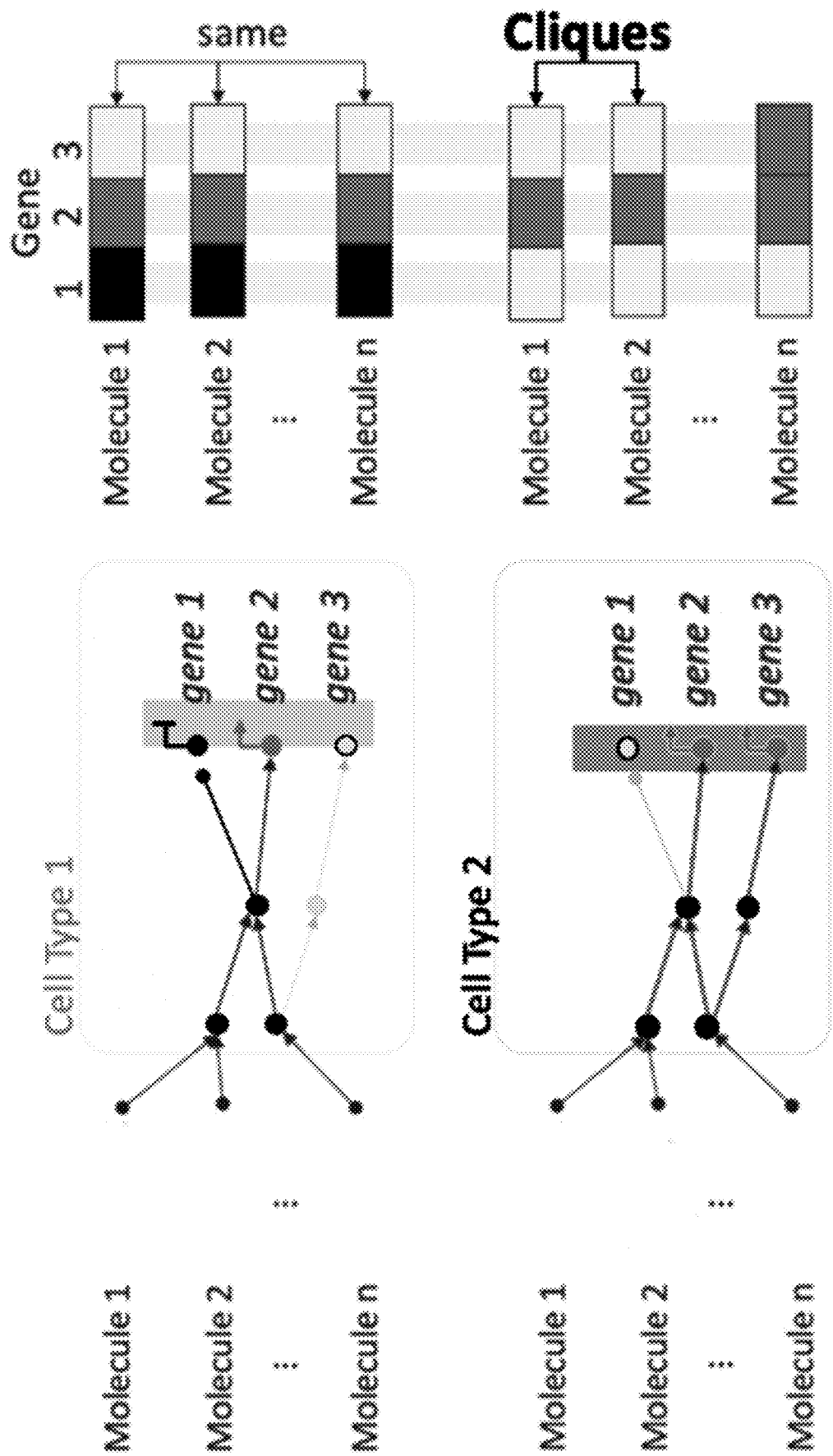
FIG. 4 illustrates insights provided by methods for associating a test compound with a compound property, in accordance with various embodiments of the present disclosure.

For instance, as illustrated in the upper panel of FIG. 4, three perturbagens (molecules 1, 2, and n) may affect a similar transcriptional response in a first cell type (cell type 1), despite targeting different molecules in the cell. As illustrated in FIG. 4, molecules 1 and 2 affect a first cellular constituent involved in upstream activation of a first signaling pathway that results in downstream downregulation of gene 1 expression in a first branch of the pathway and upregulation of gene 2 expression in a second branch of the pathway. Molecule n, in contrast, affects a second cellular constituent involved in upstream activation of both the first signaling pathway and a second signaling pathway that results in upregulation of gene 3 expression. However, cell type 1 is programed such that upregulation of gene 3 is blocked. Thus, challenge of cell type 1 with all three perturbagens results in the same transcriptional profile despite the different mechanisms of actions. Thus, the performance of phenotypic evaluation in a single cell type provides incomplete information about the effects of perturbagens due to cell-specific programming. This is a significant impediment for therapeutic development, as specificity is thereby sacrificed during the prediction process.

In contrast, as shown in the lower panel of FIG. 4, when a second cell type (cell type 2), in which downregulation of gene 1 expression is blocked but upregulation of gene 2 and gene n expression is not blocked, is exposed to the same three perturbagens, compound n causes a different transcriptional response than compounds 1 and 2, reflecting its different mechanism of action. Thus, improved enrichment of groups of perturbagens with similar mechanisms of action can be achieved using the systems and methods described herein, which consider the molecular response caused by perturbagens across multiple cell lines.

Advantageously, the methods and systems described herein evaluate phenotypic response across a range of cell types and analyze how different perturbagens correlate consistently across cell types. From this, groups of molecules that intervene to the same protein or highly interacting protein subnetwork, i.e., compound clusters, can be inferred.

For example, as described in Example 2, analysis of transcriptional responses caused by over 18,000 perturbagens across at least five cell lines each led to the identification clusters of perturbagens that cause similar cellular responses across different cell lines. Advantageously, these compound clusters significantly enriched for structural similarity and protein target interconnectivity. For instance, as described in Example 3, compound clusters of perturbagens had significantly higher Tanimoto coefficients than groupings of random perturbagens of the same size as the identified clusters ($p<0.001$). Similarly, as described in Example 3, compound clusters of perturbagens had significantly greater protein target interconnectivity than groupings of random perturbagens of the same size as the identified clusters ($p<0.001$).

These advantages are also seen when evaluating individual compound clusters. For instance, as described in Example 4, characterization of a compound cluster formed around Compound A1, a vitamin-D receptor agonist that was also discovered to reduce goblet cells, identified the majority (98%) of known vitamin-D receptor agonists present in a collection of over 18,000 perturbagens, which is a significant identification ($p<0.001$). Consistent with this finding, the compound cluster included many structural analogs of Compound A1. However, the compound cluster also included structurally-unrelated perturbagens having similar goblet cell reduction properties as Compound A1.

Similarly, as described in Example 5, characterization of a compound cluster formed around Compound A5, an mTOR and PI3K inhibitor, was significantly enriched for both mTOR inhibitors and PI3K inhibitors. The compound cluster also included structural analogs of Compound A5, despite that the analysis did not use any structural information for selection.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

Accordingly, in one aspect, the disclosure provides methods, and systems for performing such methods, for identifying groups of perturbagens (compound clusters) that cause similar cellular responses across different cell types. In some embodiments, the method includes obtaining one or more datasets (e.g., in electronic form) that collectively include, for each respective cell line in a plurality of cell lines, where the plurality of cell lines includes five or more cell lines, and for each respective compound in a plurality of compounds: for each respective exposure condition in a plurality of exposure conditions for the respective compound: a corresponding response signature for the respective compound in the respective cell line under the respective exposure condition, the corresponding response signature including a corresponding plurality of quantitative biomarker measurements of the respective cell line across a plurality of biomarkers upon exposure of the respective cell line to the respective compound at the respective exposure condition, where the plurality of biomarkers includes one hundred or more biomarkers. The method also includes, for each respective cell line in the plurality of cell lines, for each respective pair of compounds in the plurality of compounds, determining, for each unique combination of respective exposure conditions for the respective pair of compounds, a corresponding correlation of the corresponding plurality of quantitative biomarker measurements for the respective pair of compounds across the plurality of biomarkers, thereby determining one or more correlation values for the respective pair of compounds, and determining one or more weights for the respective pair of compounds from the one or more correlations values for the respective pair of compounds. The method than includes forming a plurality of compound clusters, each respective compound cluster representing a first respective compound in the plurality of compounds and including a corresponding subset of compounds in the plurality of compounds, where each respective compound in the corresponding subset of compounds satisfies one or more weight criteria with respect to the first respective compound.

In one aspect, the disclosure provides methods, and systems for performing such methods, for identifying groups of perturbagens (compound clusters) that cause similar cellular responses across different cell types. In some embodiments, the method includes obtaining one or more dataset (e.g., in electronic form), the one or more dataset including or collectively including: for each respective cell line in a plurality of cell lines, where the plurality of cell lines includes five or more cell lines: for each respective compound in the plurality of compounds: for each respective exposure condition in one or more exposure conditions for the respective compound: a corresponding response signature for the respective compound in the respective cell line under the respective exposure condition. The corresponding response signature comprising a corresponding plurality of quantitative biomarker measurements of the respective cell line across a plurality of biomarkers upon exposure of the respective cell line to the respective compound at the respective exposure condition, where the plurality of biomarkers includes one hundred or more biomarkers. The method also includes, for each respective cell line in the plurality of cell lines, for each respective pair of compounds in the plurality of compounds: (i) determining, for each unique combination of respective exposure conditions for the respective pair of compounds, a corresponding correlation of the corresponding plurality of quantitative biomarker measurements for the respective pair of compounds across the plurality of biomarkers, thereby determining a respective plurality of correlation values for the respective pair of compounds in the respective cell line, (ii) determining a respective plurality of weights for the respective pair of compounds in the respective cell line from the plurality of correlations values for the respective pair of compounds in the respective cell line, and (iii) identifying a corresponding subset of the respective plurality of weights for the respective pair of compounds in the respective cell line, where each respective weight in the corresponding subset of the plurality of weights satisfies one or more significance criteria. The method also includes determining, for each respective pair of compounds in the plurality of pairs of compounds, a corresponding comparison score from the respective subsets of the plurality of weights for the respective pair of compounds across the plurality of cell lines. The method then includes forming a plurality of compound clusters, each respective compound cluster in the plurality of compound clusters representing a respective compound in the plurality of compounds and comprising a corresponding subset of compounds in the plurality of compounds, where each respective compound in the corresponding subset of compounds satisfies one or more comparison score criteria with respect to the respective compound.

In one aspect, the disclosure provides methods, and systems for performing such methods, for identifying a property of a test perturbagen based on comparison of the test perturbagen with one or more perturbagens identified in one or more same compound clusters as the test perturbagen, e.g., as formed according to a method disclosed herein.

In one aspect, the disclosure provides methods, and systems for performing such methods, for identifying one or more perturbagen having a similar activity as a query perturbagen based on co-clustering of perturbagens with the query perturbagen in one or more same compound clusters as the test perturbagen, e.g., as formed according to a method disclosed herein.

In one aspect, the disclosure provides a method for repurposing a test pharmaceutical compound by identifying a new therapeutic use of the pharmaceutical compound based on co-clustering of the pharmaceutical compound with one or more other pharmaceutical compositions having a known and different pharmaceutical use than the test pharmaceutical compound in one or more same compound clusters as the test pharmaceutical composition, e.g., as formed according to a method disclosed herein Advantageously, the present disclosure further provides various systems and methods that improve the elucidation of a property of a perturbagen based on identification of other perturbagens that cause highly correlated cellular responses across a range of cell types by improving the training and use of a model for determining correlations between changes in cellular constituent responses. The complexity of a machine learning model includes time complexity (running time, or the measure of the speed of an algorithm for a given input size n), space complexity (space requirements, or the amount of computing power or memory needed to execute an algorithm for a given input size n), or both. Complexity (and subsequent computational burden) applies to both training of and prediction by a given model.

In some instances, computational complexity is impacted by implementation, incorporation of additional algorithms or cross-validation methods, and/or one or more parameters (e.g., weights and/or hyperparameters). In some instances, computational complexity is expressed as a function of input size n, where input data is the number of instances (e.g., the number of training samples), dimensions p (e.g., the number of features), the number of trees $n_{trees}$ (e.g., for methods based on trees), the number of support vectors $n_{sv}$ (e.g., for methods based on support vectors), the number of neighbors k (e.g., for k nearest neighbor algorithms), the number of classes c, and/or the number of neurons n at a layer i (e.g., for neural networks). With respect to input size n, then, an approximation of computational complexity (e.g., in Big O notation) denotes how running time and/or space requirements increase as input size increases. Functions can increase in complexity at slower or faster rates relative to an increase in input size. Various approximations of computational complexity include but are not limited to constant (e.g., $O(1)$), logarithmic (e.g., $O(\log n)$), linear (e.g., $O(n)$), loglinear (e.g., $O(n \log n)$), quadratic (e.g., $O(n^2)$), polynomial (e.g., $O(n^c)$), exponential (e.g., $O(c^n)$), and/or factorial (e.g., $O(n!)$). In some instances, simpler functions are accompanied by lower levels of computational complexity as input sizes increase, as in the case of constant functions, whereas more complex functions such as factorial functions can exhibit substantial increases in complexity in response to slight increases in input size.

Computational complexity of machine learning models can similarly be represented by functions (e.g., in Big O notation), and complexity may vary depending on the type of model, the size of one or more inputs or dimensions, usage (e.g., training and/or prediction), and/or whether time or space complexity is being assessed. For example, complexity in decision tree algorithms is approximated as $O(n^2 p)$ for training and $O(p)$ for predictions, while complexity in linear regression algorithms is approximated as $O(p^2 n + p^3)$ for training and $O(p)$ for predictions. For random forest algorithms, training complexity is approximated as $O(n^2 p n_{trees})$ and prediction complexity is approximated as $O(p n_{trees})$. For gradient boosting algorithms, complexity is approximated as $O(npn_{trees})$ for training and $O(pn_{trees})$ for predictions. For kernel support vector machines, complexity is approximated as $O(n^2 p + n^3)$ for training and $O(n_{sv} p)$ for predictions. For naïve Bayes algorithms, complexity is represented as $O(np)$ for training and $O(p)$ for predictions, and for neural networks, complexity is approximated as $O(pn_1 + n_1 n_2 + \ldots)$ for predictions. Complexity in K nearest neighbors algorithms is approximated as $O(knp)$ for time and $O(np)$ for space. For logistic regression algorithms, complexity is approximated as $O(np)$ for time and $O(p)$ for space. For logistic regression algorithms, complexity is approximated as $O(np)$ for time and $O(p)$ for space.

As described above, for machine learning models, computational complexity determines the scalability and therefore the overall effectiveness and usability of a model (e.g., a classifier) for increasing input, feature, and/or class sizes, as well as for variations in model architecture. In the context of large-scale datasets, as in the case of gene expression datasets comprising quantitative biomarker measurements of at least 10, at least 100, at least 1000 or more biomarkers obtained for at least 10, at least 100, at least 1000 or more cells, the computational complexity of functions performed on such large datasets may strain the capabilities of many existing systems. In addition, as the number of input features (e.g., number of biomarkers (e.g., genes)) and/or the number of instances (e.g., number of exposure conditions, cell types, and perturbagens) increases together with technological advancements, increasing availability of annotations, and expanding downstream applications and possibilities, the computational complexity of any given model can quickly overwhelm the time and space capacities provided by the specifications of a respective system.

Thus, by using a model with a minimum input size (e.g., at least 10, at least 20, at least 100 or more perturbagens; at least 10, at least 50, at least 100 or more quantitative biomarker measurements; and/or at least 5, at least 10, at least 50 or more exposure conditions) and/or a corresponding minimum number of parameters (e.g., corresponding to every possible comparison between exposure conditions for a pair of perturbagens tested in the same cell line) for identification of a property of a given perturbagen, the computational complexity is proportionally increased such that it cannot be mentally performed, and the method addresses a computational problem. For example, in an embodiment of the present disclosure, obtaining comparisons between sets of at least 100 quantitative biomarker measurements for each combination of at least 10 exposure conditions in each of at least 5 cell lines and each unique pair of at least 50 different perturbagens includes performance of 612,500 correlations (10^2*5*50C2) between sets of 100 values.

Additional details on computational complexity in machine learning models are provided in "Computational complexity of machine learning algorithms," published Apr. 16, 2018, available online at: thekerneltrip.com/machine/learning/computational-complexity-learning-algorithms; Hastie, 2001, *The Elements of Statistical Learning*, Springer, New York; and Arora and Barak, 2009, *Computational Complexity: A Modern Approach*, Cambridge University Press, New York; each of which is hereby incorporated herein by reference in its entirety.

The foregoing description, for purpose of explanation, has been described with reference to specific implementations. However, the illustrative discussions below are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

Definitions

The terminology used herein is for the purpose of describing particular implementations only and is not intended to be limiting of the claims. As used in the description of the implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

Furthermore, when a reference number is given an "$i^{th}$" denotation, the reference number refers to a generic component, set, or embodiment. For instance, a cellular-component termed "cellular-component i" refers to the $i^{th}$ cellular-component in a plurality of cellular-components.

As used herein, the term "cellular constituent" is a gene, a gene product (e.g., an mRNA and/or a protein), a carbohydrate, a lipid, an epigenetic feature, a metabolite, and/or a combination thereof. In some embodiments, each cellular constituent in a plurality of cellular constituents is a particular gene, a particular mRNA associated with a gene, a carbohydrate, a lipid, an epigenetic feature, a metabolite, a protein, or a combination thereof. In some embodiments, a plurality of cellular constituents includes nucleic acids, including DNA, modified (e.g., methylated) DNA, RNA, including coding (e.g., mRNAs) or non-coding RNA (e.g., sncRNAs), proteins, including post-transcriptionally modified protein (e.g., phosphorylated, glycosylated, myristilated, etc. proteins), lipids, carbohydrates, nucleotides (e.g., adenosine triphosphate (ATP), adenosine diphosphate (ADP) and adenosine monophosphate (AMP)) including cyclic nucleotides such as cyclic adenosine monophosphate (cAMP) and cyclic guanosine monophosphate (cGMP), other small molecule cellular constituents such as oxidized and reduced forms of nicotinamide adenine dinucleotide (NADP/NADPH), and any combinations thereof.

As used herein, the term "perturbation" in reference to a cell (e.g., a perturbation of a cell or a cellular perturbation) refers to any treatment of the cell with one or more compounds. These compounds can be referred to as "perturbagens." In some embodiments, the perturbagen can include, e.g., a small molecule, a biologic, a protein, a protein combined with a small molecule, an ADC, a nucleic acid, such as an siRNA or interfering RNA, a cDNA over-expressing wild-type and/or mutant shRNA, a cDNA over-expressing wild-type and/or mutant guide RNA (e.g., Cas9 system or other gene editing system), or any combination of any of the foregoing.

As used herein, the term "cell line" refers to a cell type. In some embodiments, a cell line refers to eukaryotic cells of a primary tissue type from an organism (e.g., a mammal such as a human), eukaryotic cells of a cultured cell line originating from a single tissue type from an organism (e.g., a mammal such as a human), or eukaryotic cells of a cultured cell line of a unicellular organism (e.g., yeast or fungi). Generally, otherwise isogenic cell lines containing a genetic or epigenetic modification (e.g., a genetic modification introduced by site-specific means, such as CRISPR, or epigenetic modification, such as induced by siRNA challenge) are considered different cell lines. In some embodiments, a cell line refers to cells of a primary cancerous tissue or cells of an immortalized cancer cell line (e.g., HeLa cells, Jurkat cells, A549 cells, etc.). Generally, the cell lines used to generate the data for the methods described herein are eukaryotic cell lines, but the disclosure is not limited to eukaryotic cell lines, Accordingly, in some embodiments, a cell line refers to cells of a cultured cell line of a unicellular prokaryotic organism (e.g., a bacterium).

As used herein, the terms "response signature," "perturbagen response signature," and "response signature caused by a perturbagen" interchangeably refer to a set of phenotypic measurements for a cell line following exposure of the cell line to a perturbagen. In some embodiments, a response signature is a set of phenotypic measurements of a single type of biomarker, e.g., only mRNA expression measurements, only measurements of cell morphogenic features, etc. In some embodiments, a response signature includes phenotypic measurements for a plurality of types of biomarkers, e.g., for mRNA expression measurements and measurements of cell morphogenic features.

As used herein, the term "exposure condition" refers to an experimental condition including an aliquot of cells, a chemical environment, a culture medium, a concentration of a perturbagen, and a length of exposure of the perturbagen to the aliquot of cells. As such, a substantial change to any one of these parameters generates a different exposure condition. For instance, all other conditions being held the same, a first assay including 5 mM of a first perturbagen constitutes a different exposure condition than a second assay including 500 mM of the first perturbagen.

As used herein, the term "measure of central tendency" refers to a central or representative value for a distribution of values. Non-limiting examples of measures of central tendency include an arithmetic mean, weighted mean, midrange, midhinge, trimean, geometric mean, geometric median, Winsorized mean, median, and mode of the distribution of values.

As used herein the term "fingerprint" as in a fingerprint of a compound is a digital digest of the compound. Nonlimiting examples of such a digital digest include Daylight fingerprints, a BCI fingerprint, an ECFC4 fingerprint, an ECFP4 fingerprint, an EcFC fingerprint, an MDL fingerprint, an atom pair fingerprint (APFP fingerprint), a topological torsion fingerprint (TTFP) fingerprint, a UNITY 2D fingerprint, an RNNS2S fingerprint, or a GraphConv fingerprint. See Franco, 2014, "The Use of 2D fingerprint methods to support the assessment of structural similarity in orphan drug legislation," J. Cheminform 6, p. 5, and Rensi and Altman, 2017, "Flexible Analog Search with Kernel PCA Embedded Molecule Vectors," Computational and Structural Biotechnology Journal, doi:10.1016/j.csbj.2017.03.003, each of which is hereby incorporated by reference. See also Raymond and Willett, 2002, "Effectiveness of graph-based and fingerprint-based similarity measures for virtual screening of 2D chemical structure databases," Journal of Computer-Aided Molecular Design 16, 59-71, and Franco et al., 2014, "The use of 2D fingerprint methods to support the assessment of structural similarity in orphan drug legislation" Journal of chemoinformatics 6(5), each of which is hereby incorporated by reference.

The foregoing description includes example systems, methods, techniques, instruction sequences, and computing machine program products that embody illustrative implementations. For purposes of explanation, numerous specific details are set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like.

The language used in the specification has been principally selected for readability and instructional purposes, and it may not have been selected to delineate or circumscribe the described subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

Any terms not directly defined herein shall be understood to have the meanings commonly associated with them as understood within the art of the invention. Certain terms are discussed herein to provide additional guidance to the practitioner in describing the compositions, devices, methods and the like of aspects of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the aspects of the invention herein.

Exemplary System Embodiments

Now that an overview of some aspects of the present disclosure and some definitions used in the present disclosure have been provided, details of an exemplary system are described in conjunction with FIGS. 1A-1E.

FIGS. 1A-1E collectively provide a block diagram illustrating a system 100 in accordance with some embodiments of the present disclosure. The system 100 identifies groups of compounds (compound clusters) which cause similar phenotypic responses when exposed to different cell types. In FIGS. 1A-1E, the system 100 is illustrated as a computing device. Of course, other topologies of the computer system 100 are possible. For instance, in some embodiments, the system 100 can in fact constitute several computer systems that are linked together in a network, or be a virtual machine or a container in a cloud computing environment. As such, the exemplary topology shown in FIGS. 1A-1E merely serves to describe the features of an embodiment of the present disclosure in a manner that will be readily understood to one of skill in the art.

Figure 1A:
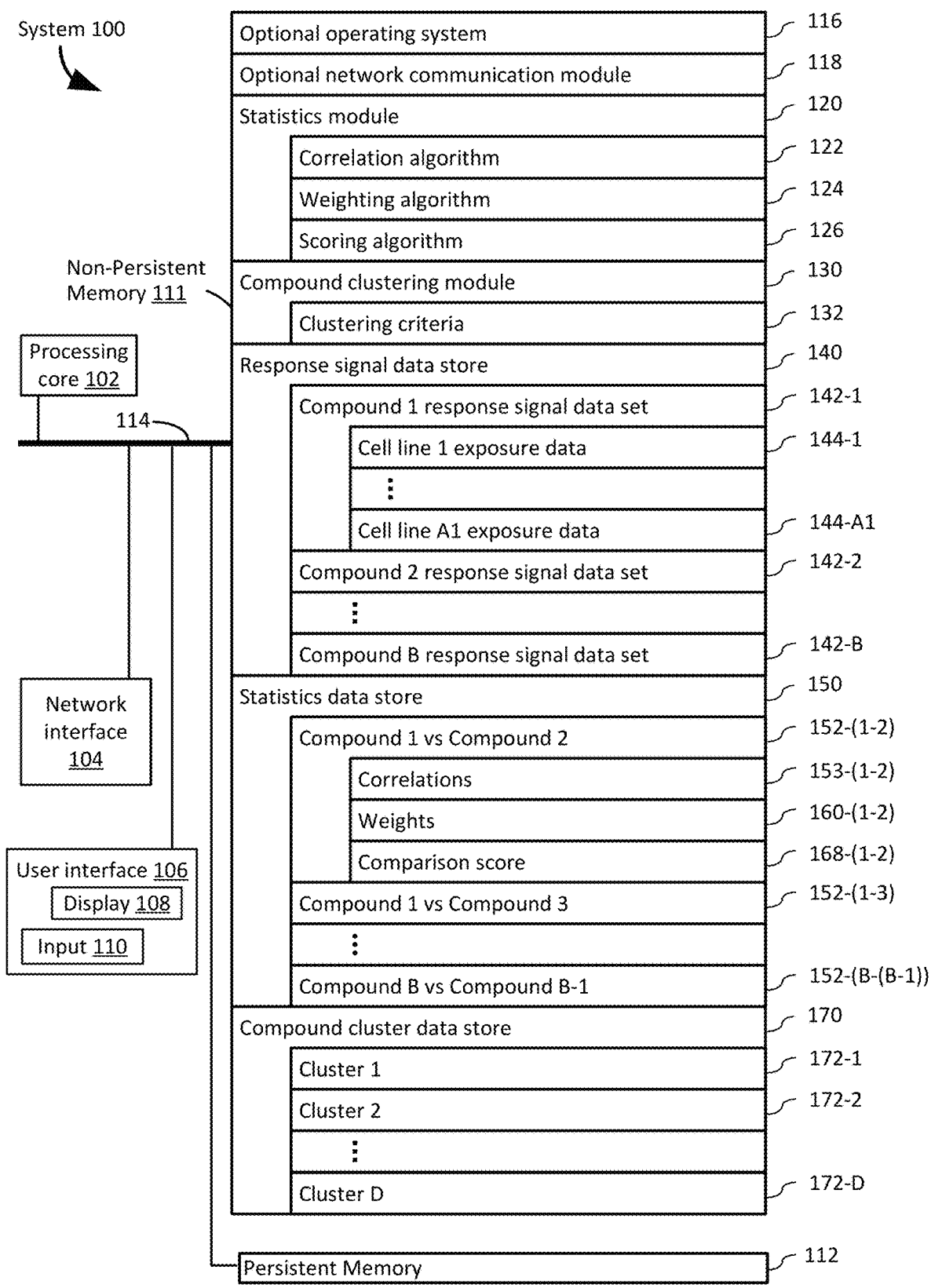

Referring to FIG. 1A, in some embodiments a computer system 100 (e.g., a computing device) includes a network interface 104. In some embodiments, the network interface 104 interconnects the system 100 computing devices within the system with each other, as well as optional external systems and devices, through one or more communication networks (e.g., through optional network communication module 118). In some embodiments, the network interface 104 optionally provides communication through optional network communication module 118 via the Internet, one or more local area networks (LANs), one or more wide area networks (WANs), other types of networks, or a combination of such networks.

Examples of networks include the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

The system 100 in some embodiments includes one or more processing units (CPU(s)) 102 (e.g., a processor, a processing core, etc.), one or more network interfaces 104, a user interface 106 including (optionally) a display 108 and an input system 110 (e.g., an input/output interface, a keyboard, a mouse, etc.) for use by the user, memory (e.g., non-persistent memory 111, persistent memory 112), and one or more communication buses 114 for interconnecting the aforementioned components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, include non-transitory computer readable storage medium. In some embodiments, the non-persistent memory 111 or alternatively the non-transitory computer readable storage medium stores the following programs, modules and data structures, or a subset thereof, sometimes in conjunction with the persistent memory 112:

- an optional operating system 116 (e.g., ANDROID, iOS, DARWIN, RTXC, LINUX, UNIX, OS X, WINDOWS, or an embedded operating system such as VxWorks), which includes procedures for handling various basic system services and for performing hardware dependent tasks;
- an optional network communication module (or instructions) 118 for connecting the system 100 with other devices and/or a communication network;
- a statistics module 120, including:
  - a correlation algorithm 122 for determining a correlation 156 between perturbagen response signatures 146 measured in a common cell line in a unique combination of exposure conditions (e.g., correlation $156_{(i-1)j(m-n)}$ between the response signatures for (i) perturbagen i in cell line j under exposure condition m, and (ii) perturbagen l in cell line j under exposure condition n);
  - a weighting algorithm 124 for determining a weight 164 for the correlation between a response signature 146 for a first perturbagen measured under a unique exposure condition in a cell line and response signatures 146 for a second perturbagen measured under a plurality of exposure conditions in the same cell line (e.g., weight $164_{(l-i)jk}$ for the correlation between (i) response signature $146_{ijk}$ for perturbagen i in cell line j under exposure condition k, and (ii) response signatures $146_{lj1}$ to $146_{ljT}$ for perturbagen l in cell line j under all measured exposure conditions); and
  - a scoring algorithm 126 for determining a comparison score 168 for the correlation between perturbagen response signatures 146 measured under different exposure conditions across a plurality of cell lines (e.g., comparison score 168(l-i) for the correlation between (i) response signatures 146 for compound i under all exposure conditions across all cell lines, and (ii) response signatures 146 for compound l under all exposure conditions across all cell lines);
- a compound clustering module 130 for identifying groups of compounds (compound clusters 172) that produce highly correlated response signatures across multiple cell lines, according to a set of clustering criteria 132;
- a response signature data store 140 for storing response signature data sets 142 for a plurality of perturbagens, where each response signature data set 142 includes exposure data sets 144 measured across different exposure conditions and different cell lines for a perturbagen, where each exposure data set includes measurements 148 for a plurality of biomarkers;
- a statistics data store 150 for storing summary statistic sets 152 for the comparison of response signatures caused by two perturbagens across a plurality of cell lines, the summary statistics including:
  - a set of correlations 153 for the comparison of response signatures caused by each perturbagen against every other perturbagen, including a subset of correlations 154 for each cell line in which both perturbagens was tested against, where each subset 154 includes a correlation 156 determined for each unique combination of exposure conditions under which the pair of perturbagens was tested;

a set of weights 160 for the comparison of response signatures caused by each perturbagen against every other perturbagen, including a subset of weights 162 for each cell line in which both perturbagens was tested against, where each subset 162 includes a weight 164 representing the correlation between (i) the response signature caused by a first perturbagen under a first exposure condition in a respective cell line, and (ii) each response signature caused by a second perturbagen under each exposure condition in the respective cell line; and a comparison score 168 representing the correlation between perturbagen response signatures 146 measured under different exposure conditions across a plurality of cell lines; and a compound cluster data store 170 for storing records of compound clusters 172, e.g., identified using compound clustering module 130, where each compound cluster record 172 includes the identity of a plurality of perturbagens 174 that cause response signatures across multiple cell lines that are highly correlated with response signatures caused by a seeding perturbagen.

In various embodiments, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations. In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of the system 100, that is addressable by the system 100 so that the system 100 may retrieve all or a portion of such data when needed.

Although FIGS. 1A-1E depict a "system 100," the figures are intended more as a functional description of the various features that may be present in computer systems than as a structural schematic of the implementations described herein. In practice, and as recognized by those of ordinary skill in the art, items shown separately could be combined and some items could be separated. Moreover, although FIGS. 1A-1E depict certain data and modules in non-persistent memory 111, some or all of these data and modules instead may be stored in persistent memory 112 or in more than one memory. For example, in some embodiments, at least dataset store 120 is stored in a remote storage device which can be a part of a cloud-based infrastructure. In some embodiments, at least dataset store 120 is stored on a cloud-based infrastructure. In some embodiments, dataset store 120 and signature store 140 can also be stored in the remote storage device(s).

II. Exemplary Method Embodiments

A system 100 in accordance with various embodiments of the present disclosure is described above with reference to FIGS. 1A-1E. Method 300 for identifying groups of perturbagens that cause highly correlated phenotypic responses across different cellular contexts, e.g., to associate a test compound with a compound property, which may be performed using system 100 described above, is detailed below with reference to FIGS. 3A-3D, in accordance with various embodiments of the present disclosure.

Generally, method 300 includes obtaining response signatures for each of a plurality of perturbagens following exposure of the perturbagens to multiple cell lines under multiple exposure conditions, and then determining which groups of perturbagens cause highly correlated response signatures across different cell lines, thereby identifying groupings of compounds—"compound clusters"—that affect cellular pathways in a similar fashion, e.g., that have common mechanisms of action ("MoA") for affecting a phenotypic change in cell. The compound clusters identified using method 300 have many uses in the field of pharmaceutical drug discovery and rationale drug design. For instance, in one embodiment, one or more property of a test compound can be inferred from the properties of one or more other compounds identified in one or more of the same compound clusters as the test compound. In another embodiment, one or more compounds having the same desired property as a query compound can be identified based on identification of one or more compound clusters containing the query compound. In another embodiment, a repurposed use of a test compound can be identified based upon the properties of one or more other compounds identified in one or more of the same compound clusters as the test compound.

Input Data

Referring to FIG. 3A, method 300 includes obtaining (302) one or more datasets in electronic form (e.g., compound response data sets 142-1 to 142-B stored in system 100 as shown in FIGS. 1A-1E). The one or more datasets include or collectively include, for each respective cell line in a plurality of cell lines (e.g., cell lines 1 to $A_p$, for each compound Br), e.g., five or more cell lines, for each respective compound in a plurality of compounds (e.g., compounds 1 to B), and for each respective exposure condition in a plurality of exposure conditions (e.g., exposure conditions 1 to $F_p$ for each compound $B_p$) for the respective compound: a corresponding response signature for the respective compound in the respective cell line under the respective exposure condition (e.g., response signature 146-1-1-1 for compound 1 exposed to cell line 1 under exposure condition 1, as illustrated in FIG. 1A). The corresponding response signature including a corresponding plurality of quantitative biomarker measurements of the respective cell line across a plurality of biomarkers upon exposure of the respective cell line to the respective compound at the respective exposure condition (e.g., biomarker measurements 148-1-1-1-1 to 148-1-1-1-E for biomarkers 1 to E measured following exposure of cell line 1 to compound 1 under exposure condition 1), e.g., where the plurality of biomarkers includes one hundred or more biomarkers.

Figure 1B:
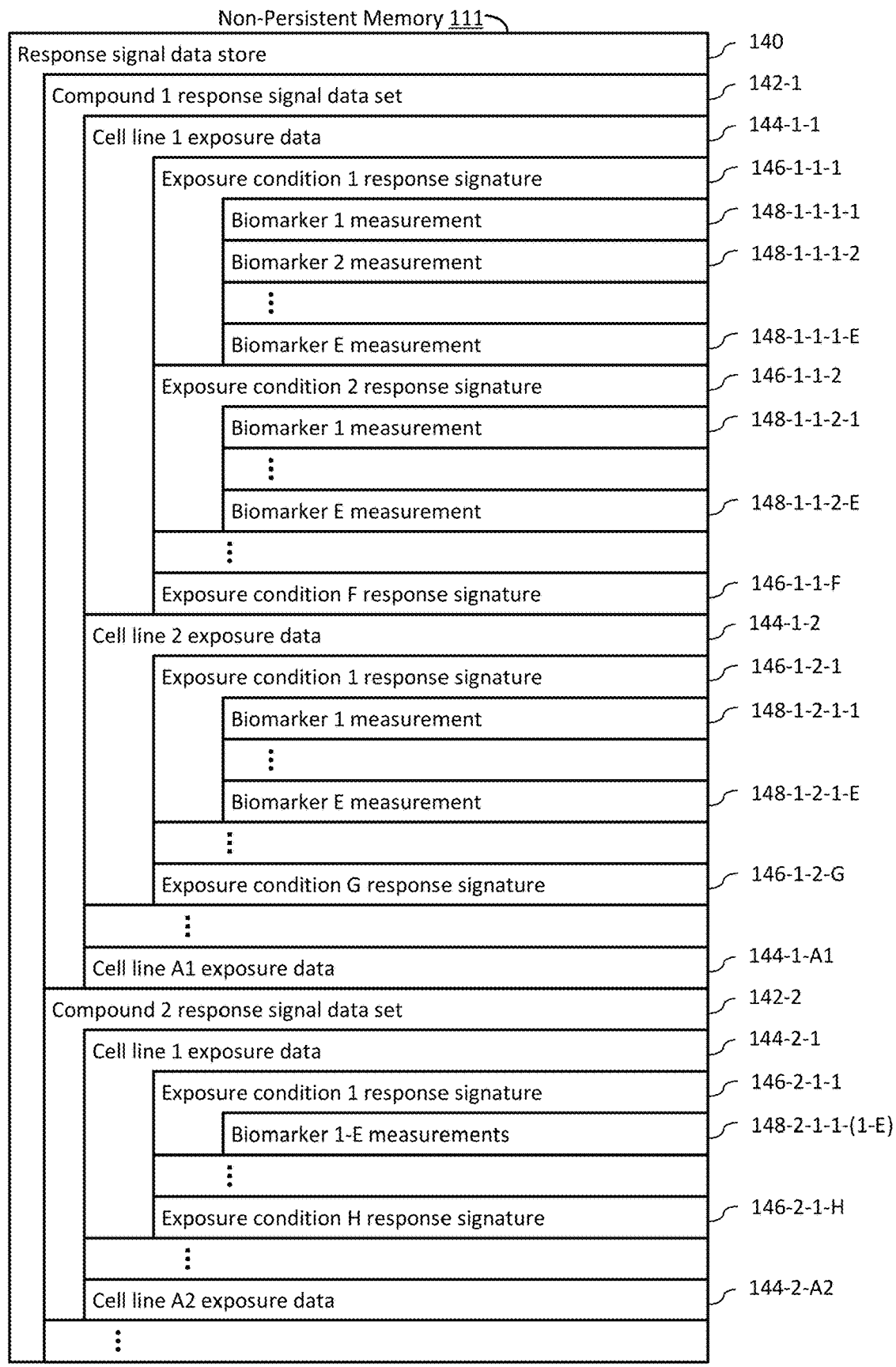

For instance, as collectively illustrated in FIGS. 1A and 1B, an example dataset stored in response data store 140 includes response datasets 142-1 to 142-B for compounds 1 to B. Each response dataset 142 includes exposure data 144 collected following exposure of the respective compound to one of a plurality of cell lines. For instance, as illustrated in FIG. 1B, exposure data 144-1-1 to 144-1-A1 represent response signatures measured following exposure of each of cell lines 1 to A1 to compound 1 under a plurality of exposure conditions (e.g., exposure conditions 1 to F for cell line 1, exposure conditions 1 to G for cell line 2, etc.). The response signatures include measurements for a plurality of biomarkers of the cell line. For instance, as illustrated in FIG. 1B, the response signature 146-1-1-1 for exposure of cell line 1 to compound 1 under exposure condition 1 includes measurements 148-1-1-1-1 to 148-1-1-1-E for biomarkers 1 to E (e.g., mRNA expression levels, cell morphogenic features, etc.).

While FIG. 1B illustrates an example data set in which the same set of biomarkers is measured for each compound, tested against each cell line, at each exposure condition, it is not required that the same set of biomarkers are measured for each compound, each cell line, or each condition. Rather, the only requirement is that there is a significant overlap between the biomarkers measured in each response signature being compared. For example, consider the scenario shown in Table 1, where the response signatures for compound 1 ("C1") and compound 2 ("C2") after exposure to cell line 1 ("L1"), cell line 2 ("L2"), and cell line 3 ("L3") under different exposure conditions ("E$") are being compared. The biomarkers measured for each experiment are indicated with an "x".

TABLE 1

Example comparison of compounds 1 and 2.

| | Biomarkers | | | | | | | | | |
|---|---|---|---|---|---|---|---|---|---|---|
| | 1 | 2 | 3 | 4 | 5 | 6 | 7 | 8 | 9 | 10 |
| C1/L1/E1 | x | x | x | | x | x | x | | x | x |
| C1/L1/E2 | x | x | x | | x | x | x | | x | x |
| C1/L2/E3 | x | x | x | | x | x | x | | x | x |
| C1/L2/E4 | x | x | x | | x | x | x | | x | x |
| C1/L3/E5 | | x | x | x | x | | x | x | x | x |
| C1/L3/E6 | | x | x | x | x | | x | x | x | x |
| C2/L1/E7 | x | x | x | | x | x | x | | x | x |
| C2/L1/E8 | x | x | x | | x | x | x | | x | x |
| C2/L2/E9 | x | | x | x | x | x | x | | | x |
| C2/L2/E10 | x | | x | x | x | x | x | | | x |
| C2/L3/E11 | x | x | | x | x | x | x | | x | x |
| C2/L3/E12 | | x | x | x | x | | x | x | | x |

Referring to Table 1, the response signatures for exposure of compound 1 to cell lines 1 and 2, under each of exposure conditions 1-4, have measurements for the same set of biomarkers (biomarkers 1, 2, 3, 5, 6, 7, 9, and 10), but the response signatures for exposure of compound 1 to cell line 3, under exposure conditions 5 and 6, have measurements for a different set of biomarkers (biomarkers 2, 3, 4, 5, 7, 8, 9, and 10). The response signatures for exposure of compound 2 to cell line 1, under exposure conditions 7 and 8, have measurements for the same set of biomarkers as do the response signatures for exposure of compound 1 to cell line 1. But, the response signatures for exposure of compound 2 to cell line 2, under exposure conditions 9 and 10, have measurements for a different set of biomarkers as do the response signatures for exposure of compound 1 to cell line 2. Further, the response signature for exposure of compound 2 to cell line 3 under exposure condition 11 has measurements for a different set of biomarkers than the response signature for exposure of compound 2 to cell line 3 under exposure condition 12, and both of these response signatures have measurements for different sets of biomarkers than the response signature for exposure of compound 1 to cell line 3, under conditions 5 and 6. Nonetheless, analysis of the correlation between response signatures caused by compounds 1 and 2 can be performed according to the methods described herein.

In some embodiments a compound of the present disclosure is a chemical compound that satisfies the Lipinski rule of five criterion. In some embodiments, a compound of the present disclosure is an organic compounds that satisfies two or more rules, three or more rules, or all four rules of the Lipinski's Rule of Five: (i) not more than five hydrogen bond donors (e.g., OH and NH groups), (ii) not more than ten hydrogen bond acceptors (e.g. N and O), (iii) a molecular weight under 500 Daltons, and (iv) a Log P under 5. The "Rule of Five" is so called because three of the four criteria involve the number five. See, Lipinski, 1997, Adv. Drug Del. Rev. 23, 3, which is hereby incorporated herein by reference in its entirety. In some embodiments, a compound of the present disclosure satisfies one or more criteria in addition to Lipinski's Rule of Five. For example, in some embodiments, a compound of the present disclosure has five or fewer aromatic rings, four or fewer aromatic rings, three or fewer aromatic rings, or two or fewer aromatic rings. A compound is an example of a perturbagen.

The datasets 142 obtained for perturbagen response signatures 146 are generally stored in a digital format in a persistent memory (e.g., persistent memory 112 of FIG. 1A) of a computing device (e.g., system 100 of FIGS. 1A-1E), however they may be loaded into active memory (e.g., non-persistent memory 111 of FIGS. 1A-1E) as needed in order to carry out the remaining steps described herein. Generally, the remaining steps of the process of FIGS. 3A-3D are carried out by one or more computing devices (e.g., system 100 of FIG. 1A-IE). An example computing device is discussed with respect to FIG. 1A-IE. However, in practice the process of FIGS. 3A-3D may contain additional interstitial or follow on steps that may be conducted outside of a computer.

Normalization

In some embodiments, the methods described herein include one or more normalization step. In some embodiments, normalization is applied internally within a particular response signature. For example, referring to method 300 illustrated in FIGS. 3A-3D, in some embodiments, each corresponding response signature 146 (e.g., a response signature 146-$i$-$j$-$k$ for a set of biomarker measurements 148 collected following expose of compound i to a cell line j under an exposure condition k, as illustrated in FIG. 1B) is normalized (304) against a response signature (e.g., quantitative biomarker measurements) of one or more control biomarkers (e.g., control genes) in the respective cell line.

In some embodiments, the control biomarkers are of the same type of biomarker as the quantitative biomarker measurements being normalized in the response signature. For instance, in some embodiments, where a response signature includes a plurality of mRNA expression values for a set of test genes, the mRNA expression values are normalized against mRNA expression values for a set of control genes. In some embodiments, where more than one type of biomarker is used in a response signature for the exposure of a compound to a cell line, more than one set of control biomarkers, corresponding to the different types of biomarkers measured in the response signature, are used to normalize the response signature. For instance, in some embodiments, where a response signature includes a plurality of mRNA expression values for a set of test genes and a plurality of cell morphology values for a set of cell morphology features, the mRNA expression values for the set of test genes are normalized against mRNA expression values for a set of control genes and the cell morphology values for the set of cell morphology features are normalized against cell morphology values for a set of control cell morphology features. Generally, control biomarkers are selected because they are relatively invariant across cell lines and/or are not significantly affected by exposure of a cell line to a perturbagen. For instance, in some embodiments, a control gene is constitutively expressed at a stable level across many different cell lines.

In some embodiments, that are not mutually exclusive with the normalization schemes described above, normalization is applied across multiple response signals 146, e.g., to control for batch effects across a set of experiments. For example, in some embodiments, a control experiment is performed along with a set of test experiments, and biomarker measurements from the control experiment are used to normalize response signatures 146 for the test experiments. For example, in some embodiments, where a particular cell line is exposed to a plurality of perturbagens and/or to a particular perturbagen under a plurality of exposure conditions, a control experiment can measure a control response signature for a cell line that is not exposed to a perturbagen (e.g., a negative control) and/or a control response signature for a cell line that is exposed to a control perturbagen under a control condition. The control response signature can include quantitative biomarker measurements for the same set of biomarkers as the test experiments or can include quantitative biomarker measurements for a different set of biomarkers as the test experiments.

In some embodiments, the normalization technique, applied across a single experiment and/or across a batch of experiments, is a rescaling normalization. Also known as a min-max normalization, rescaling normalization rescales the range of values in the response signature, or the range of values in a subset of values for a single type of biomarker in the response signature. In some embodiments, a rescaling normalization divides the difference between a particular value and the minimum value for a set of values by the difference between the maximum and minimum value in the set of values. Other methods for performing rescaling normalization are known in the art.

In some embodiments, the normalization technique, applied across a single experiment and/or across a batch of experiments, is a measure of central tendency (e.g., a mean) normalization. This type of normalization uses a measure of central tendency for a value to transform the values of a response signature. For instance, in some embodiments, a mean normalization determines a difference between a particular value and the mean of all values in a set of values, and then divides the difference by the difference between the maximum and minimum value in the set of values. Other methods for performing measure of central tendency normalization are known in the art.

In some embodiments, the normalization technique, applied across a single experiment and/or across a batch of experiments, is a standardization. In some embodiments, standardization divides the difference between a particular value and the mean of all values in a set of values by a measure of dispersion (e.g., a standard deviation) for the set of values. Other methods for performing standardization are known in the art.

Cell Lines

The systems and methods described herein rely upon measurements of response signatures across a plurality of cell lines in order to control for cell-specific responses. That is, by expanding the analysis across an increasing number of different cell types, the correlations identified between response signatures better reflects the portion of the responses that unique to the compounds because effects caused by cell-specific programming are diluted across the data set.

In some embodiments, the plurality of cell lines used for a method described herein includes at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 40, at least 50, or more cell lines. Referring specifically to method 300 illustrated in FIGS. 3A-3D, in some embodiments, the plurality of cell lines used for a method described herein includes (306) at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or more cell lines.

In some embodiments, the plurality of cell lines used for a method described herein includes no more than 10,000 cell lines, no more than 5000 cell lines, no more than 2500 cell lines, no more than 1000 cell lines, no more than 500 cell lines, no more than 250 cell lines, no more than 100 cell lines, or fewer cell lines.

In some embodiments, the plurality of cell lines used for a method described herein includes from 5 to 10,000 cell lines, from 5 to 5000 cell lines, from 5 to 2500 cell lines, from 5 to 1000 cell lines, from 5 to 500 cell lines, from 5 to 250 cell lines, from 5 to 100 cell lines, from 10 to 10,000 cell lines, from 10 to 5000 cell lines, from 10 to 2500 cell lines, from 10 to 1000 cell lines, from 10 to 500 cell lines, from 10 to 250 cell lines, from 10 to 100 cell lines, from 25 to 10,000 cell lines, from 25 to 5000 cell lines, from 25 to 2500 cell lines, from 25 to 1000 cell lines, from 25 to 500 cell lines, from 25 to 250 cell lines, or from 25 to 100 cell lines.

Accordingly, in some embodiments, the systems and methods described herein use data sets generated across a plurality of cell lines, e.g., at least 5 cell lines. However, this does not mean that the response data used for each compound must be generated using the same plurality of cell lines. Rather, it only means that, in order to compare the response signatures of two compounds x and y, the data set includes response signatures generated by exposing a minimal number of cell lines to both compounds x and y. That is, where the plurality of cell lines is at least 5 cell lines, the data set includes response signatures generated by the exposure of compound x to at least cell lines 1, 2, 3, 4, and 5, under a plurality of exposure conditions each, and response signatures generated by the exposure of compound y to at least cell lines 1, 2, 3, 4, and 5, under a plurality of exposure conditions each.

In some embodiments, the plurality of cell lines used to generate the response signatures used in the methods described herein includes eukaryotic cells of a primary tissue type from an organism (e.g., a mammal such as a human), eukaryotic cells of a cultured cell line originating from a single tissue type from an organism (e.g., a mammal such as a human), or eukaryotic cells of a cultured cell line of a unicellular organism (e.g., yeast or fungi). In some embodiments, the plurality of cell lines used to generate the response signatures used in the methods described herein includes two or more otherwise isogenic cell lines containing a genetic or epigenetic modification (e.g., a genetic modification introduced by site-specific means, such as CRISPR, or epigenetic modification, such as induced by siRNA challenge) relative to each other. In some embodiments, the plurality of cell lines used to generate the response signatures used in the methods described herein includes cells of a primary cancerous tissue or cells of an immortalized cancer cell line (e.g., HeLa cells, Jurkat cells, A549 cells, etc.). In some embodiments, the plurality of cell lines used to generate the response signatures used in the methods described herein includes cells of a cultured cell line of a unicellular prokaryotic organism (e.g., a bacterium).

Compounds

The systems and methods described herein rely upon comparison of the response signatures measured for a plurality of compounds across cell lines to identify compounds have shared properties. As such, the more compounds represented in a dataset the greater the chances of finding compounds having similar properties and shared mechanisms of action.

Accordingly, in some embodiments, the plurality of compounds for which response data is used, according to the methods described herein, is at least 10 compounds. In some embodiments, the plurality of compound is at least 50, at least 100, at least 150, at least 200, at least 250, at least 500, at least 1000, at least 2500, at least 5000, at least 10,000, at least 25,000, at least 50,000, at least 100,000, at least 250,000, at least 500,000, at least 1 million, at least 2.5 million, at least 5 million, at least 10 million, at least 25 million, at least 100 million, or more. In some embodiments, the plurality of compounds is no more than 100 million, no more than 25 million, no more than 10 million, no more than 5 million, no more than 2.5 million, no more than 1 million, no more than 500,000, no more than 250,000, no more than 100,000, no more than 50,000, no more than 25,000, no more than 10,000, or fewer.

In some embodiments, the plurality of compounds is from 10 to 100 million compounds. In some embodiments, the plurality of compounds is from 10 to 10 million compounds. In some embodiments, the plurality of compounds is from 10 to 1 million compounds. In some embodiments, the plurality of compounds is from 10 to 100,000 compounds. In some embodiments, the plurality of compounds is from 10 to 10,000 compounds. In some embodiments, the plurality of compounds is from 10 to 1000 compounds. In some embodiments, the plurality of compounds is from 10 to 100 compounds. In some embodiments, the plurality of compounds is from 100 to 100 million compounds. In some embodiments, the plurality of compounds is from 100 to 10 million compounds. In some embodiments, the plurality of compounds is from 100 to 1 million compounds. In some embodiments, the plurality of compounds is from 100 to 100,000 compounds. In some embodiments, the plurality of compounds is from 100 to 10,000 compounds. In some embodiments, the plurality of compounds is from 100 to 1000 compounds. In some embodiments, the plurality of compounds is from 1000 to 100 million compounds. In some embodiments, the plurality of compounds is from 1000 to 10 million compounds. In some embodiments, the plurality of compounds is from 1000 to 1 million compounds. In some embodiments, the plurality of compounds is from 1000 to 100,000 compounds. In some embodiments, the plurality of compounds is from 1000 to 10,000 compounds. In some embodiments, the plurality of compounds is from 10,000 to 100 million compounds. In some embodiments, the plurality of compounds is from 10,000 to 10 million compounds. In some embodiments, the plurality of compounds is from 10,000 to 1 million compounds. In some embodiments, the plurality of compounds is from 10,000 to 100,000 compounds. In some embodiments, the plurality of compounds is from 100,000 to 100 million compounds. In some embodiments, the plurality of compounds is from 100,000 to 10 million compounds. In some embodiments, the plurality of compounds is from 100,000 to 1 million compounds. For example, with reference to method 300 illustrated in FIGS. 3A-3D, in some embodiments, the plurality of compounds is between 10 and $1 \times 10^8$ compounds, between 100 and $1 \times 10^7$ compounds, between 1000 and $1 \times 10^6$ compounds, or between 10,000 and 100,000 compounds (308).

Exposure Conditions

The systems and methods described herein rely upon measurements of response signatures across a plurality of exposure conditions in order to account for particular exposure conditions that are not biologically relevant, for instance exposure conditions under which a test perturbagen is inactive or at two low of a concentration to effect a significant change in the response signature of a cell line. This is particularly important in embodiments where a large number of perturbagens are being evaluated and/or one or more perturbagens being evaluated are not well characterized because biologically-relevant contexts will not be known. Accordingly, in some embodiments, each perturbagen is exposed to each cell type under at least 5 different exposure conditions. In some embodiments, each perturbagen is exposed to each cell type under at least 10, at least 15, at least 20, at least 25, at least 30, at least 40, at least 50, at least 75, at least 100, at least 150, at least 200, at least 250, at least 300, at least 400, at least 500, at least 750, at least 1000, or more different exposure conditions.

In some instances, one or more of the perturbagens being evaluated is not exposed to a particular cell line under a minimal number of exposure conditions. In some embodiments, response signatures for perturbagens not exposed to a particular cell line a minimal number of times will be excluded from the analysis. In other embodiments, these response signatures will still be used in the analysis. Accordingly, in some embodiments, at least 50%, at least 75%, at least 80%, at least 90%, at least 95%, at least 98%, or at least 99% of the plurality of perturbagens evaluated has been exposed to each cell type under at least 5, at least 10, at least 15, at least 20, at least 25, at least 30, at least 40, at least 50, at least 75, at least 100, at least 150, at least 200, at least 250, at least 300, at least 400, at least 500, at least 750, at least 1000, or more different exposure conditions.

However, the exposure conditions under which a perturbagen is exposed to one cell line do not have to be the same as the exposure conditions under which the perturbagen is exposed to another cell line. Rather, it is only that the perturbagen is exposed to each cell type under a variety of a different exposure conditions that is important. Generally, the more exposure conditions under which a particular perturbagen is exposed to a cell line the greater the chance that a biologically-relevant exposure condition will be used. Likewise, the exposure conditions under which a first perturbagen is exposed to one or more cell lines do not have to be the same as the exposure conditions under which a second perturbagen, being compared to the first perturbagen, is exposed to the same cell lines. This is because, at least in part, different ranges of exposure conditions will be biologically relevant for different perturbagens.

Generally, any change to the chemical environment, time, or concentration under which a perturbagen is exposed to cell line will represent a different exposure condition.

For example, with respect to the chemical environment under which a perturbagen is exposed to a cell line, a respective exposure condition refers to a temperature, a pH, an ionic strength, a particular chemical medium or component thereof, or a combination thereof. In some embodiments, data for the exposure of one or more perturbagen to one or more cell line includes response signatures for at least 5 different chemical environments. In some embodiments, data for the exposure of one or more perturbagen to one or more cell line includes response signatures for at least 10, at least 15, at least 20, at least 25, at least 30, at least 40, at least 50, at least 75, at least 100, at least 150, at least 200, at least 250, at least 300, at least 400, at least 500, at least 750, at least 1000, or more different chemical environments. In some embodiments, data for the exposure of each of the plurality of perturbagens analyzed includes response signatures for at least 5, at least 10, at least 15, at least 20, at least 25, at least 30, at least 40, at least 50, at least 75, at least 100, at least 150, at least 200, at least 250, at least 300, at least 400, at least 500, at least 750, at least 1000, or more different chemical environments.

Similarly, with respect to the length of time for which a perturbagen was exposed to a cell line, any significant difference in the duration of the length will represent a different exposure condition. For the purpose of clarity, unless otherwise specified herein, a difference of at least 10% in the duration of an exposure constitutes a significant change and, thus, a different exposure condition. In some embodiments, data for the exposure of one or more perturbagen to one or more cell line includes response signatures for at least 5 different exposure times. In some embodiments, data for the exposure of one or more perturbagen to one or more cell line includes response signatures for at least 10, at least 15, at least 20, at least 25, at least 30, at least 40, at least 50, at least 75, at least 100, at least 150, at least 200, at least 250, at least 300, at least 400, at least 500, at least 750, at least 1000, or more different exposure times. In some embodiments, data for the exposure of each of the plurality of perturbagens analyzed includes response signatures for at least 5, at least 10, at least 15, at least 20, at least 25, at least 30, at least 40, at least 50, at least 75, at least 100, at least 150, at least 200, at least 250, at least 300, at least 400, at least 500, at least 750, at least 1000, or more different exposure times.

Likewise, with respect to the concentration at which a perturbagen was exposed to a cell line, any significant difference in the concentration will represent a different exposure condition. For the purpose of clarity, unless otherwise specified herein, a difference of at least 10% of the concentration of the perturbagen constitutes a significant change and, thus, a different exposure condition. In some embodiments, data for the exposure of one or more perturbagen to one or more cell line includes response signatures for at least 5 different perturbagen concentrations. In some embodiments, data for the exposure of one or more perturbagen to one or more cell line includes response signatures for at least 10, at least 15, at least 20, at least 25, at least 30, at least 40, at least 50, at least 75, at least 100, at least 150, at least 200, at least 250, at least 300, at least 400, at least 500, at least 750, at least 1000, or more different perturbagen concentrations. In some embodiments, data for the exposure of each of the plurality of perturbagens analyzed includes response signatures for at least 5, at least 10, at least 15, at least 20, at least 25, at least 30, at least 40, at least 50, at least 75, at least 100, at least 150, at least 200, at least 250, at least 300, at least 400, at least 500, at least 750, at least 1000, or more different perturbagen concentrations.

Accordingly, referring to method 300 illustrated in FIGS. 3A-3D, in some embodiments, the respective exposure condition is a duration of exposure, a concentration of the respective compound, an environmental condition of the exposure, or a combination thereof (310).

Biomarkers

The systems and methods described herein rely upon measurements of a plurality of biomarkers to form response signatures that are indicative of phenotypic shifts caused by perturbation of any one of thousands of cellular pathways/ networks in cell lines following exposure to perturbagens. Accordingly, in some embodiments, each response signature 146 is formed from quantitative measurements 148 of at least 100 biomarkers. In some embodiments, each response signature is formed from quantitative measurements of at least 25, at least 50, at least 100, at least 150, at least 200, at least 250, at least 300, at least 400, at least 500, at least 750, at least 1000, at least 2500, at least 5000, at least 10,000, at least 25,000, at least 50,000, at least 75,000, at least 100,000, or more biomarkers.

Generally, when comparing the response signatures for any particular pair of exposure conditions for two perturbations, the respective response signatures have substantially overlapping sets of biomarker measurements, e.g., at least 90% overlap, at least 95% overlap, at least 98% overlap, at least 99% overlap, or complete overlap. However, the biomarkers represented in response signatures used for comparing one pair of exposure conditions do not have to match the biomarkers represented in response signatures used for comparing other pairs of exposure conditions within a particular analysis. Rather, it is a determined measure of correlation between particular pairs of exposure conditions, as determined for a sufficiently representative set of biomarkers, that is used in furtherance of the method.

Generally, any type of biomarker representative of a cellular phenotype that can be quantitatively measured can be used to form the response signatures used in the methods described herein. Non-limiting examples of types of biomarkers that find use in the present methods and systems described herein include nucleic acids, ribonucleic acids, carbohydrates, lipids, epigenetic features, metabolites, proteins, cell morphological features, and combinations thereof. Accordingly, referring to method 300 illustrated in FIGS. 3A-3D, in some embodiments the plurality of biomarkers are nucleic acids, ribonucleic acids, carbohydrates, lipids, epigenetic features, metabolites, proteins, cell morphological features, or a combination thereof (312).

In some embodiments, biomarkers of interest include nucleic acids, such as DNA, modified (e.g., methylated) DNA, RNA, including coding (e.g., mRNAs) or non-coding RNA (e.g., sncRNAs), proteins, including post-transcriptionally modified protein (e.g., phosphorylated, glycosylated, myristilated, etc. proteins), lipids, carbohydrates, nucleotides (e.g., adenosine triphosphate (ATP), adenosine diphosphate (ADP) and adenosine monophosphate (AMP)) including cyclic nucleotides such as cyclic adenosine monophosphate (cAMP) and cyclic guanosine monophosphate (cGMP), other small molecule cellular-components such as oxidized and reduced forms of nicotinamide adenine dinucleotide (NADP/NADPH), cell morphology features (e.g., as measured using imaging techniques, and any combinations thereof. In some embodiments, the biomarker measurements include gene expression measurements, such as RNA levels.

In some embodiments one or more of the biomarker measurements 148 include RNA expression data, e.g., obtained using a whole transcriptome shotgun sequencing (RNA-seq) assay that quantifies gene expression from cells (e.g., a single cell or culture of cells) in counts of transcript reads mapped to gene constructs. As such, in some embodiments, RNA-seq experiments aim at reconstructing all full-length mRNA transcripts concurrently from millions of short reads. RNA-seq facilitates the ability to look at alternative gene spliced transcripts, post-transcriptional modifications, gene fusion, mutations/SNPs and changes in gene expression over time, or differences in gene expression in different groups or treatments. See, for example, Maher et al., 2009, "Transcriptome sequencing to detect gene fusions in cancer," Nature. 458 (7234): 97-101, which is hereby incorporated by reference. In addition to mRNA transcripts, RNA-seq can evaluate and quantify individual members of different populations of RNA including total RNA, mRNA, miRNA, lncRNA, snoRNA, or tRNA within entities. As such, in some embodiments, one or more of the measured biomarkers is an abundance of a specific RNA species as determined using RNA-seq. Non-limiting examples of RNA expression techniques that can be used to generate RNA abundance measurements for use in the response signatures described herein are disclosed in Li et al., 2008, "IsoLasso: A LASSO Regression Approach to RNA-Seq Based Transcriptome Assembly," Cell 133, 523-36; Subramanian et al., "A Next Generation Connectivity Map: L1000 Platform and the First 1,000,000 Profiles," Cell 171(6), 1437; and Jiang, 2008, "Methods for evaluating gene expression from Affymetrix microarray datasets," BMC Bioinformatics 9, 284, which are incorporated herein by reference, in their entireties, for all purposes.

In some embodiments, one or more of the biomarker measurements 148 include epigenetic features, e.g., chromatin modification (e.g., DNA methylation) data, protein-chromatin association data, and chromatin accessibility data. Protein-chromatin association data can be obtained, for example, using ChIP-Seq data. See, for example, Quigley and Kintner, 2017, "Rfx2 Stabilizes Foxj 1 Binding at Chromatin Loops to Enable Multiciliated Cell Gene Expression," PLoS Genet 13, e1006538, which is incorporated herein by reference in its entirety. Chromatin accessibility data can be obtained, for example, using ATAC-seq (Assay for Transposase-Accessible Chromatin using sequencing). See, for example, Buenrostro et al., 2013, "Transposition of native chromatin for fast and sensitive epigenomic profiling of open chromatin, DNA-binding proteins and nucleosome position," Nature Methods 10, 1213-1218, which is incorporated herein by reference in its entirety for all purposes.

In some embodiments, one or more of the biomarker measurements 148 include protein abundance values. Several methods can be used for large-scale determination of protein abundance values, e.g., quantitative proteomics, including two-dimensional electrophoresis and mass spectrometry. An example method for quantitative proteomics by two-dimensional electrophoresis is disclosed in Alban et al., (2003). "A novel experimental design for comparative two-dimensional gel analysis: Two-dimensional difference gel electrophoresis incorporating a pooled internal standard," Proteomics, 3(1): 36-44, which is incorporated herein by reference, in its entirety, for all purposes. Example methods for quantitative proteomics by mass spectrometry is described in Aebersold and Mann (September 2016), "Mass-spectrometric exploration of proteome structure and function," Nature. 537 (7620): 347-55 (in bulk); and Specht et al., (2019 Jun. 9), "Single-cell mass-spectrometry quantifies the emergence of macrophage heterogeneity," doi:10.1101/665307, which are incorporated herein by reference, in its entirety, for all purposes.

In some embodiments, one or more of the biomarker measurements 148 include metabolomics data. Metabolomics is a systematic evaluation of small molecules in order to obtain biochemical insight into disease pathways. Examples methods for obtaining metabolomic data are described, for example, in Newgard et al., 2009, "A branched-chain amino acid-related metabolic signature that differentiates obese and lean humans and contributes to insulin resistance," Cell Metab 9: 311-326, 2009; Wang, 2011, "RE: Metabolite profiles and the risk of developing diabetes," Nat Med 17: 448-453, which are incorporated herein by reference, in their entireties, for all purposes.

In some embodiments, one or more of the biomarker measurements 148 include post-translational protein modifications. Mass spectrometric peptide sequencing, optionally using one or more isotope labeling strategies, can be used to generate post-translational protein modification data. See, for example, Mann and Jensen, 2003 "Proteomic analysis of post-translational modifications," Nature Biotechnology 21, 255-261, which is hereby incorporated by reference.

In some embodiments, one or more biomarker measurements are made in bulk, i.e., based on measurements of the biomarker in a plurality of cells of the same cell line exposed to the same perturbagen under the same exposure condition, for example co-cultured in a single well. In some embodiments, one or more biomarker measurements are made from a single cell. Examples of techniques for measuring biomarker values in single cells include, but are not limited to single-cell ribonucleic acid (RNA) sequencing (scRNA-seq), scTag-seq, single-cell assay for transposase-accessible chromatin using sequencing (scATAC-seq), CyTOF/SCoP, E-MS/Abseq, miRNA-seq, CITE-seq, and any combination thereof. The measurement technique can be selected based on the type of biomarker to be measured. For instance, scRNA-seq, scTag-seq, and miRNA-seq can be used to measure RNA expression. Specifically, scRNA-seq measures expression of RNA transcripts, scTag-seq allows detection of rare mRNA species, and miRNA-seq measures expression of micro-RNAs. CyTOF/SCoP and E-MS/Abseq can be used to measure protein expression in the cell. CITE-seq simultaneously measures both gene expression and protein expression in the cell, and scATAC-seq measures chromatin conformation in the cell. Table 2 below provides example protocols for performing each of the cellular constituent abundance measurement techniques described above.

TABLE 2

Example Measaurement Protocols

| Technique | Protocol |
|---|---|
| RNA-seq | Olsen et al., (2018), "Introduction to Single-Cell RNA Sequencing," Current protocols in molecular biology 122(1), pg. 57. |
| Tag-seq | Rozenberg et al., (2016), "Digital gene expression analysis with sample multiplexing and PCR duplicate detection: A straightforward protocol," BioTechniques, 61(1), pg. 26. |
| ATAC-seq | Buenrostro et al., (2015), "ATAC-seq: a method for assaying chromatic accessibility genome-wide," Current protcols in molecular biology, 109(1), pg. 21. |
| miRNA-seq | Faridani et al., (2016), "Single-cell sequencing of the small-RNA transcriptome," Nature biotechnology, 34(12), pg. 1264. |
| CyTOF/SCoPE-MS/Abseq | Bandura et al., (2009), "Mass cytometry: technique for real time single cell multitarget immunoassay based on inductivitely coupled plasma time-of-flight mass spectrometry," Analystic chemistry, 81(16), pg. 6813. Budnik et al., (2018), "SCoPE-ME: mass scpectrometry of single mammalian cells quantifies proteome heterogenity during cell differentiation," Genome biology, 19(1), pg. 161. Shahi et al., (2017), "Abseq: Ultrahigh-throughoutput single cell protein profiling with droplep microfluidic barcoding," Scientific reports, 7, pg. 44447. |
| CITE-seq | Stoeckius et al., (2017), "Simultaneous epitope and transcritome measurement in single cells," Nature Methods, 14(9), pg. 856. |

The biomarker measurement technique used may result in cell death. Alternatively, cellular-components may be measured by extracting out of the live cell, for example by extracting cell cytoplasm without killing the cell. Techniques of this variety allow the same cell to be measured at multiple different points in time.

In some embodiments, one or more of the biomarker measurements 148 is a morphological feature of a cell, or an enumerated portion of a cell, e.g., determined by optical measurement of the cell or portion thereof. Example morphological features include, but are not limited to cell area, cell perimeter, cell aspect ratio, actin content, actin texture, cell solidity, cell extent, cell nuclear area, cell nuclear perimeter, cell nuclear aspect ratio, and algorithm-defined features (e.g., latent features). Other examples of morphological features are described in Table S2 of Gustafsdottir et al., PLoS ONE 8(12): e80999. doi:10.1371/journal.pone.0080999 (2013), which is incorporated herein by reference, in its entirety for all purposes. Example methods for measuring optical features of cell morphology features are described, for example, in Carpenter et al., 2006, "CellProfiler: image analysis software for identifying and quantifying cell phenotypes," Genome Biol. 7, R100 PMID: 17076895; Kamentsky et al., 2011, which is incorporated herein by reference, in its entirety, for all purposes.

In some embodiments, one or more of the biomarker measurements 148 is a latent feature extracted from cellular imaging data. Latent features cannot be measured directly and, therefore, have to be derived from the empirical measurements. In some embodiments, a latent feature is an arithmetic combination of two or more direct measurements of the cell line. For instance, a weighted average of three different morphological features of the cell measured by cellular imaging. In some embodiments, a latent feature is identified by a deep learning model. For example, latent features extracted from label-free live cell images using an adversarial auto-encoding deep convolutional neural network were shown to allow classification of melanoma cell states. See, for example, Zaritsky et al., "Interpretable deep learning of label-free live cell images uncovers functional hallmarks of highly-metastatic melanoma," bioRxiv 2020, which is incorporated herein by reference in its entirety for all purposes.

In some embodiments, one or more of the biomarker measurements 148 include a cell morphological feature measured using cell painting. Cell painting is a morphological profiling assay that multiplexes fluorescent dyes, imaged in multiple channels, to reveal broadly relevant cellular components or organelles. Cells are plated in multiwell plates, perturbed with the treatments to be tested, stained, fixed, and imaged on a high-throughput microscope. Next, automated image analysis software identifies individual cells and measures any number between one and tens of thousands (but most often approximately 1,000) morphological features (various measures of size, shape, texture, intensity, etc. of various whole-cell and sub-cellular components) to produce a profile that is suitable for the detection of even subtle phenotypes. Profiles of cell populations treated with different experimental perturbations can be compared to suit many goals, such as identifying the phenotypic impact of chemical or genetic perturbations, grouping compounds and/or genes into functional pathways, and identifying signatures of disease. See, for example, Bray et al., 2016, Nature Protocols 11, 1757-1774.

Thus, referring to method 300 illustrated in FIGS. 3A-3D, in some embodiments, each quantitative biomarker measurement in the corresponding plurality of quantitative biomarker measurement is a colorimetric measurement, a fluorescence measurement, a luminescence measurement, or a resonance energy transfer (FRET) measurement.

Pairwise Correlation of Response Signatures

Having obtained one or more datasets (e.g., compound response data sets 142-1 to 142-B stored in system 100 as shown in FIGS. 1A-IE) with response signatures 146 for a plurality of exposure conditions under which a plurality of compounds were exposed to a plurality of cell lines, as described above, method 300 then includes determining a measure of correlation between the response signatures measured following exposure of the compounds to different cell lines, in order to identify compounds that cause similar phenotypic responses across a range of cellular contexts. For example, referring to FIG. 4, while some compounds will cause similar phenotypic responses when exposed to a single cell type (e.g., molecules 1, 2, and n cause similar phenotypic responses in cell type 1, as illustrated in FIG. 4), they may cause different phenotypic responses in other cell types (e.g., molecules 1 and 2 cause different phenotypic responses in cell type 2, as illustrated in FIG. 4, reflecting variability in both the compound responses and the difference in the cellular programing of cell types 1 and 2).

First, response signatures caused by the exposure of different compounds to a common cell line are compared in a pair-wise fashion. Because biologically relevant exposure conditions may vary for each compound, and may not be known when performing exposure assays, response signatures 146 for exposure of a first compound to a first cell line are not simply compared to a single corresponding response signature for exposure of the second compound to the first cell line. Rather, each of a plurality of response signatures 146 from exposure of a first compound to a respective cell line under different exposure conditions are compared to each of a plurality of response signatures 146 from exposure of the second compound to the respective cell line under different exposure conditions. For example, referring to FIG. 2A, each of response signatures 246-1-1-1 to 246-1-1-F (measured for exposure of compound 1 to cell line 1 under exposure conditions 1 to F) is compared to each of response signatures 246-2-1-1- to 246-2-1-H (measured for exposure of compound 2 to cell line 2 under exposure conditions 1 to H, where exposure conditions 1 to F and 1 to H may be the same set or different sets of exposure conditions), to generate F×H comparisons 256-(1-2)-1-(f-h) (for comparison of compound 1 to compound 2 in cell line 1 under respective conditions f (for compound 1) and h (for compound 2). While these comparisons are illustrated as a matrix 254-(1-2)-1 in FIG. 2A, the data structure(s) used in practice may vary. For example, each row and/or column illustrated in matric 254-(1-2)-1 may be stored separately in system 100.

In some embodiments, each comparison generates a measure of correlation 156 between each pair of response signatures, e.g., a correlation coefficient. Non-limiting examples of correlation types that find use in the methods and systems described herein includes Pearson's correlation (see, for example, Rodgers and Nicewander (1988), "Thirteen ways to look at the correlation coefficient," The American Statistician, 42(1): 59-66, which is incorporated herein by reference, in its entirety, for all purposes), distance correlation (see, for example, Székely and Bakirov, Annals of Statistics, 35 (6): 2769-94 (2007), which is incorporated herein by reference, in its entirety, for all purposes), randomized dependence (see, for example, Lopez-Paz et al., "The Randomized Dependence Coefficient," arXiv: 1304.7717 (2013), which is incorporated herein by reference, in its entirety, for all purposes), correlation ratio (see, for example, Crathorne, A R, "Calculation of the Correlation Ratio," Journal of the American Statistical Association, 394-396 (1922), which is incorporated herein by reference, in its entirety, for all purposes), entropy-based mutual information (see, for example, Dionisio, A., Menezes, R. & Mendes, D. A. "Entropy-Based Independence Test," Nonlinear Dyn., 44:351-57 (2006), which is incorporated herein by reference, in its entirety, for all purposes), total correlation (see, for example, Watanabe, 1960, "Information theoretical analysis of multivariate correlation", IBM Journal of Research and Development 4, 66-82, which is incorporated herein by reference, in its entirety, for all purposes), dual total correlation (see, for example, Han, 1978, "Nonnegative entropy measures of multivariate symmetric correlations, Information and Control" 36, 133-156, which is incorporated herein by reference, in its entirety, for all purposes), and polychoric correlation (see, for example, Drasgow, 1986, "Polychoric and polyserial correlations," in Kotz, Samuel, Narayanaswamy Balakrishnan, Campbell B. Read, Brani Vidakovic & Norman L. Johnson (Eds), Encyclopedia of Statistical Sciences 7. New York, NY: John Wiley, pp. 68-74, which is incorporated herein by reference, in its entirety, for all purposes).

Figure 2A:
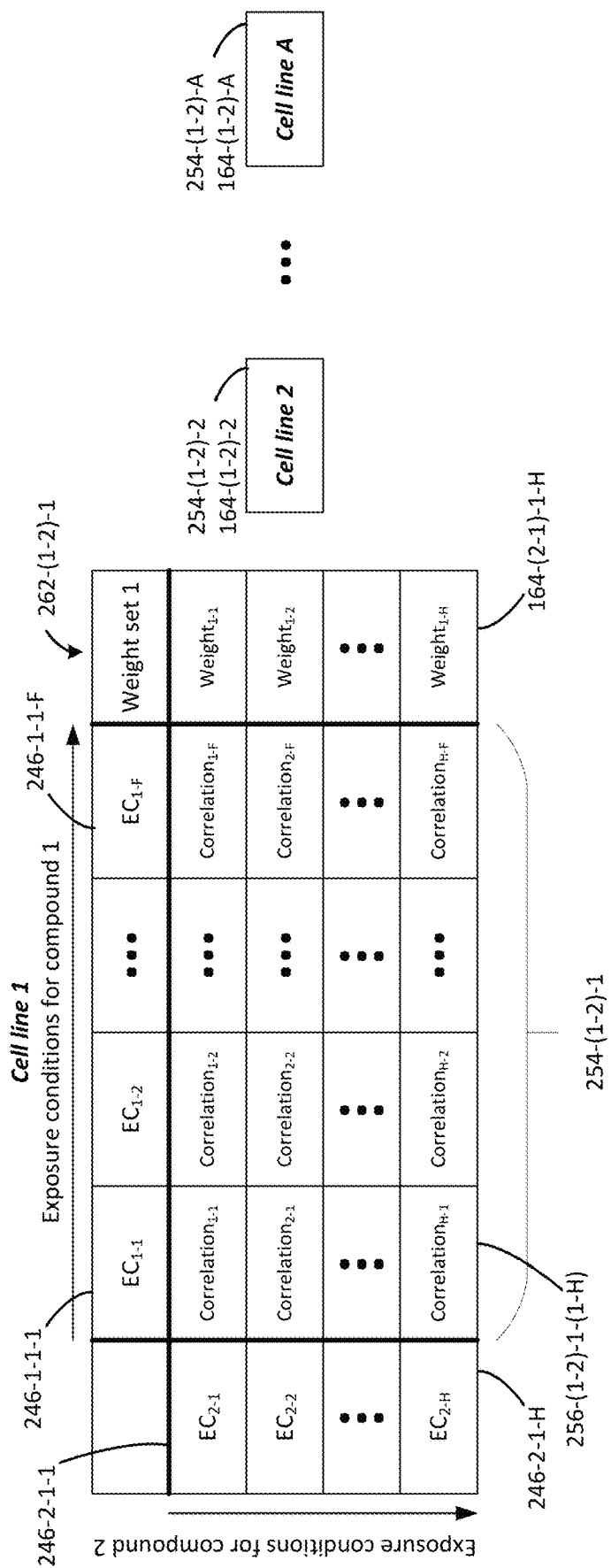
FIGS. 2A, 2B, and 2C collectively illustrate example data structures and analysis for associating a test compound with a compound property, in accordance with various embodiments of the present disclosure.
Figure 2B:
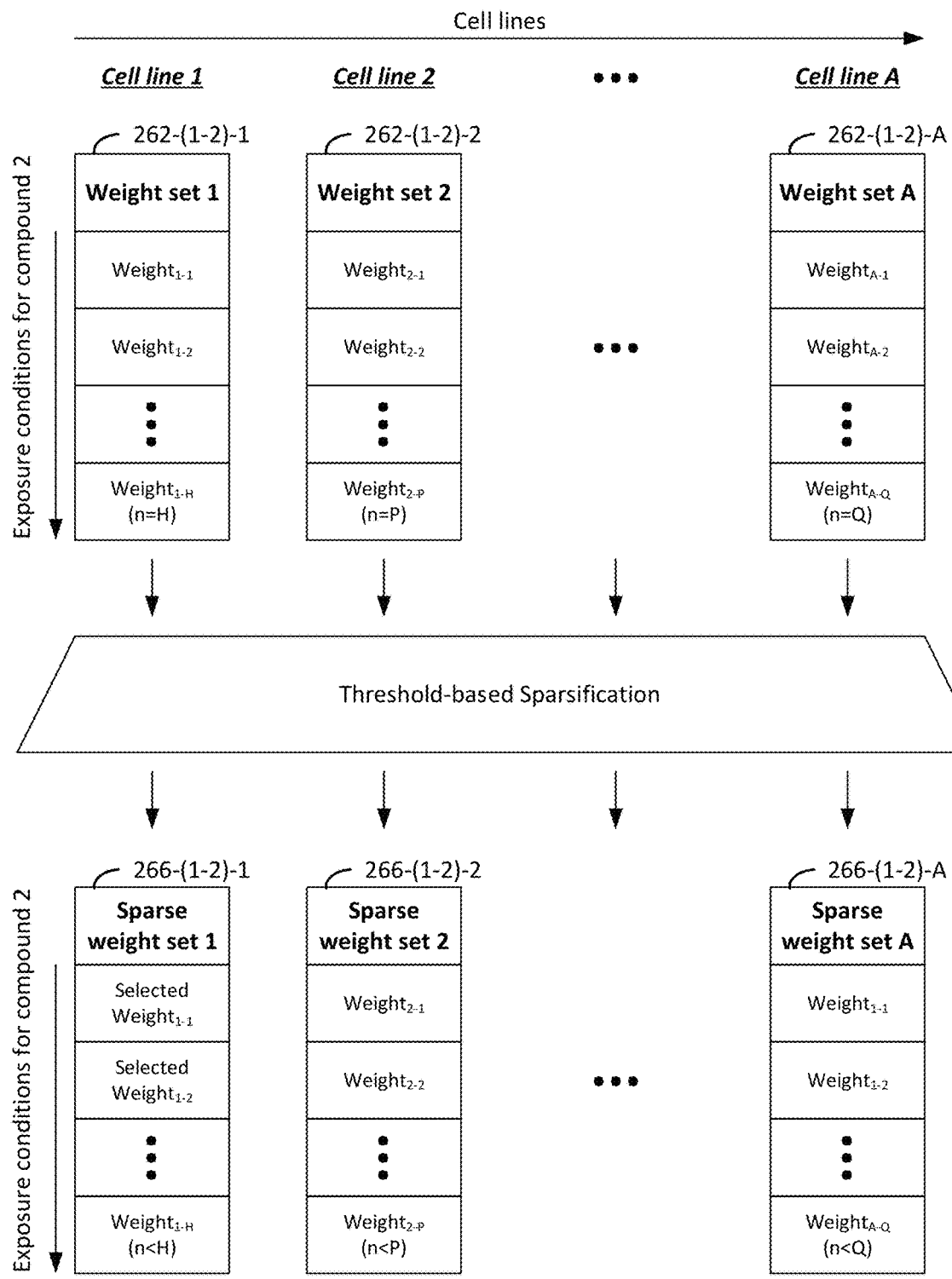
Figure 2C:
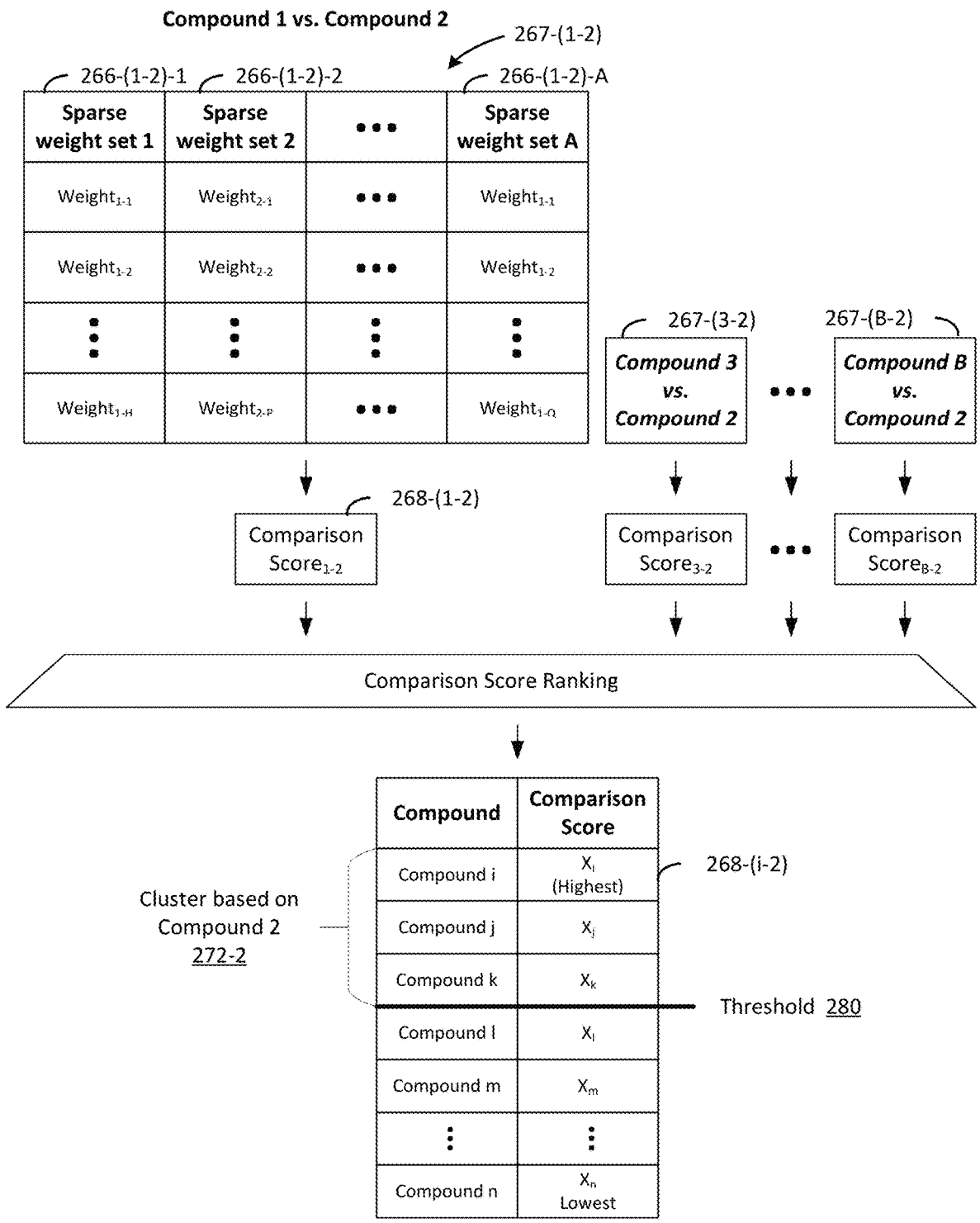
Figure 3D:
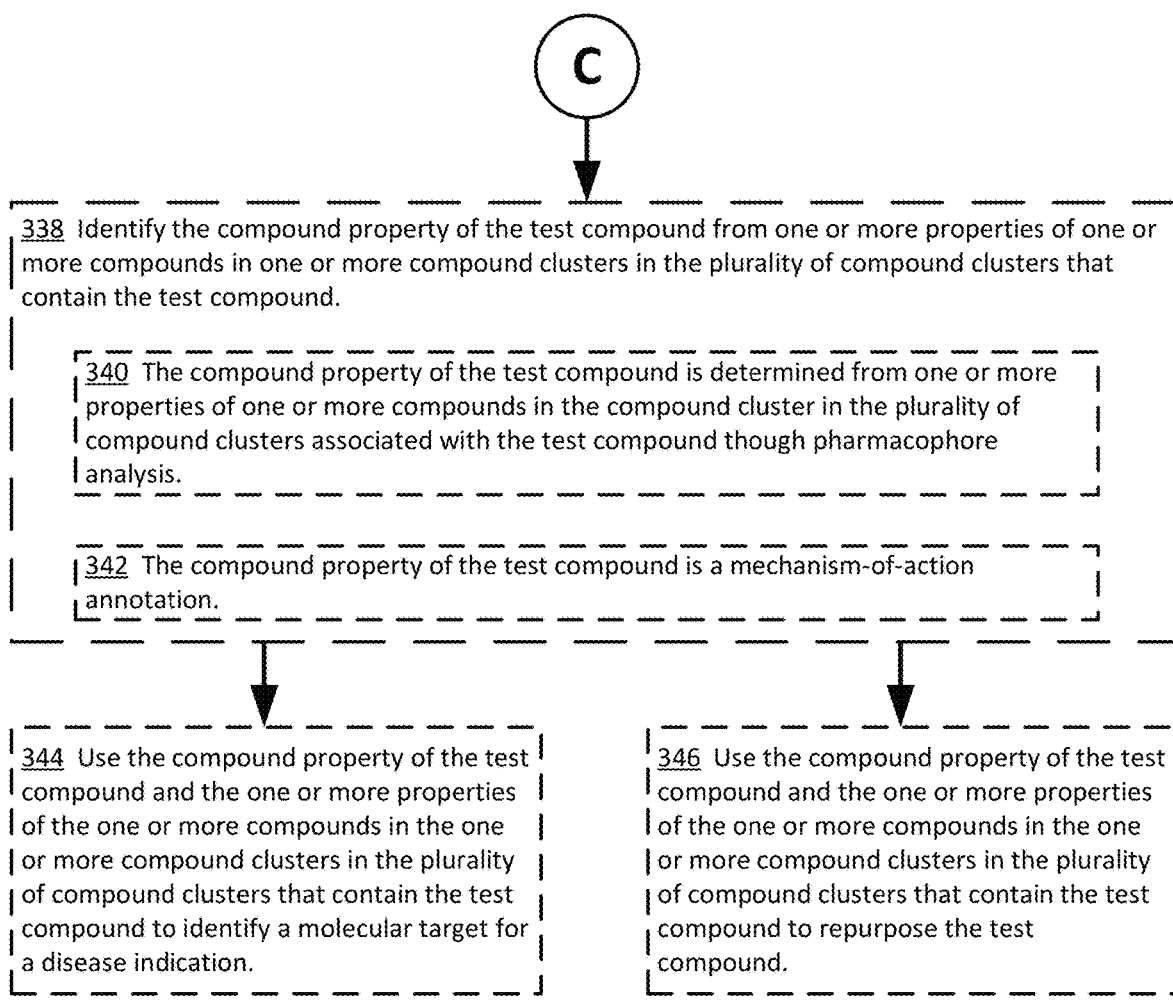

Accordingly, with reference to method 300 in FIGS. 3A-3D, in some embodiments, the method includes, for each respective cell line in the plurality of cell lines (e.g., each of cell lines 1 to A, as depicted in FIG. 2A), for each respective pair of compounds in the plurality of compounds (316) (e.g., each of compounds 1 to B, as depicted in FIG. 2C), determining (318) for each unique combination of respective exposure conditions for the respective pair of compounds, a corresponding correlation 156 (e.g., comparisons 256-(1-2)-1-(f-h), as depicted in FIG. 2A) of the corresponding plurality of quantitative biomarker measurements 148 for the respective pair of compounds across the plurality of biomarkers, thereby determining a plurality of correlation values 152 for the respective pair of compounds (e.g., matrices 254-(1-2)-1 . . . 254-(1-2)-A for comparison of the response signatures of compounds 1 and 2 across each of cell lines 1 to A, as depicted in FIG. 2A). In some embodiments, the corresponding correlation is a Pearson's correlation distance correlation, randomized dependence, correlation ratio, entropy-based mutual information, total correlation, dual total correlation, or polychoric correlation. In some embodiments, referring to method 300, the corresponding correlation of the corresponding plurality of quantitative biomarker measurements for the respective pair of compounds across the plurality of biomarkers is a Pearson correlation (322).

Weighting of Compound Comparisons

Figure 1D:
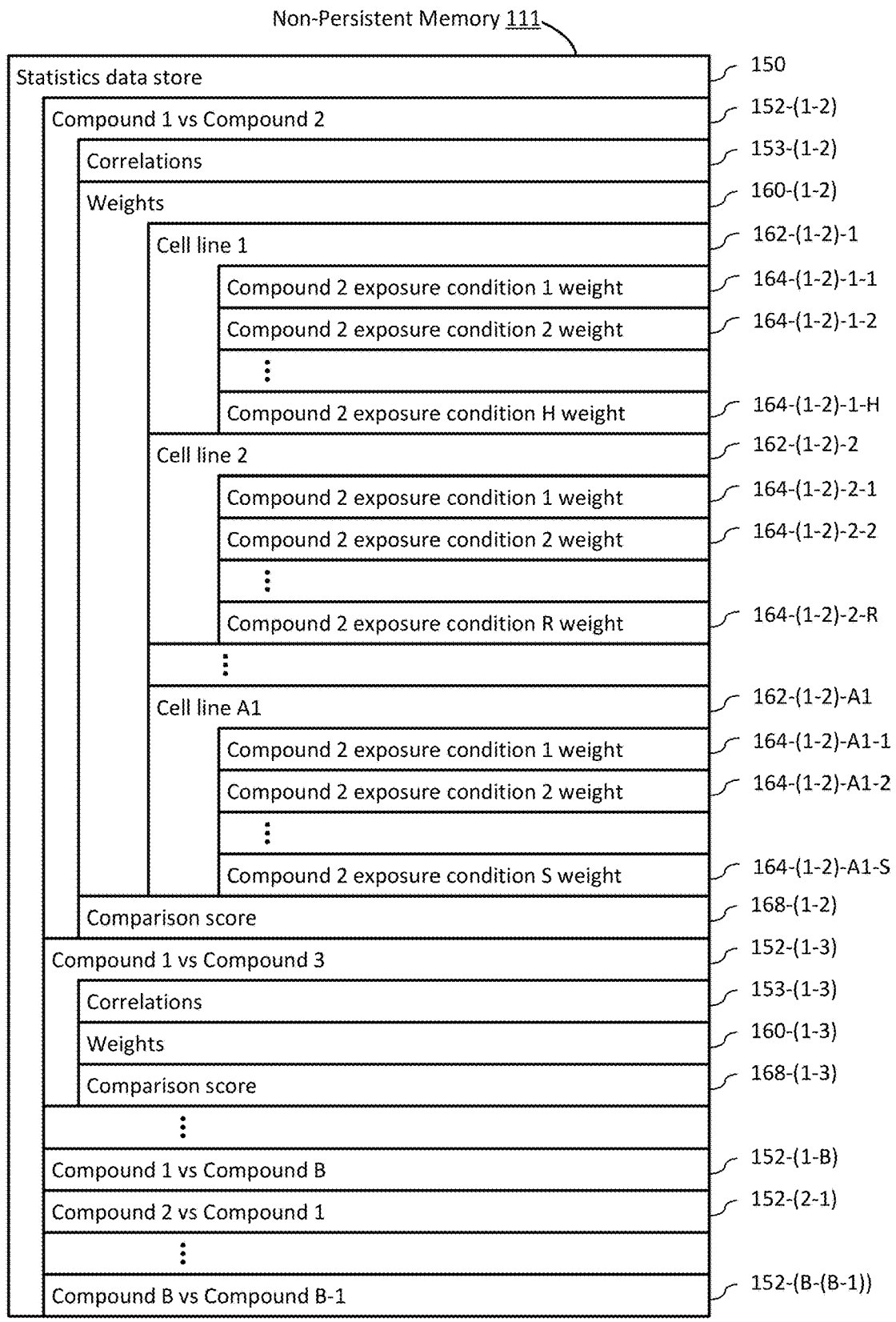
Figure 1E:
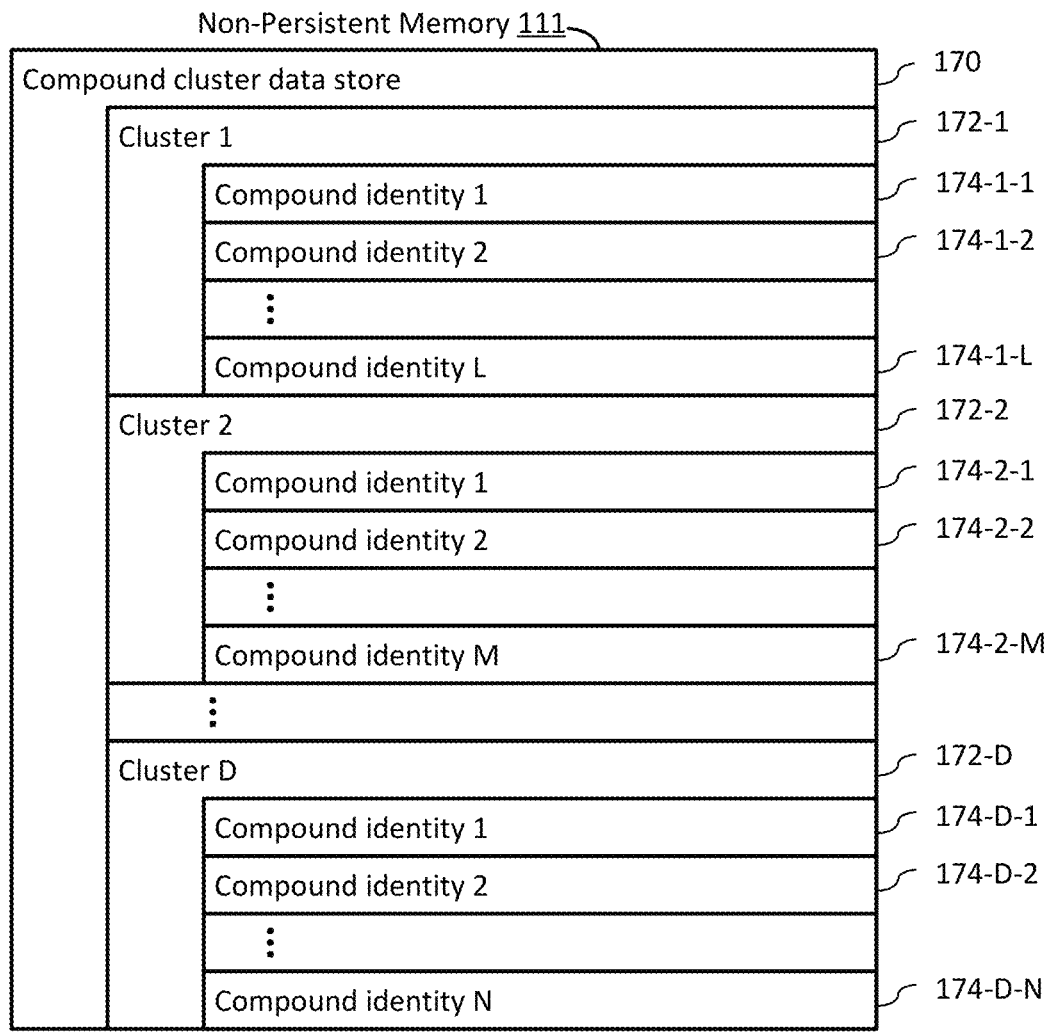

Having obtained individual measures of correlation 156 (e.g., correlations 256 for the comparison of compound 1 to compound 2 in cell line 1, as illustrated in FIG. 2A) for pairwise comparisons of response signatures 146 obtained following exposure of different compounds to different cell lines under different exposure conditions, one or more weights 160 is generated to summarize these individual correlations for the comparison of two respective compounds. Accordingly, with reference to method 300 in FIGS. 3A-3D, in some embodiments, the method includes determining (324) one or more weights 160 (e.g., weights 164 as illustrated in FIGS. 1D and 2A, respectively) for the respective pair of compounds from the one or more correlations values 156 for the respective pair of compounds.

In some embodiments, the weighting is a measure of central tendency of the individual correlations 156 represented by the weight. In some embodiments, the measure of central tendency is an arithmetic mean, weighted mean, midrange, midhinge, trimean, geometric mean, geometric median, Winsorized mean, median, and mode of the distribution of correlations 156 represented by the weight. In some embodiments, a respective weight of the one or more weights 160 is a mean of the correlations 156 represented by the weight.

However, recognizing that not every exposure condition under which a compound is exposed to a cell line will be biologically relevant, in some embodiments, a weight (e.g., weight 164) is generated from only a subset of the correlations 156 represented by the weight.

In some embodiments, a respective weight (e.g., weight 164) is the top correlation within the set of all correlations represented by the weight. For example, referring to FIG. 2A, weight 164-(2-1)-1-H represents the correlations (e.g., correlations H-1 through H-F) between (i) the response signature for exposure of compound 2 to cell line 1 under exposure condition H, and (ii) the response signatures for exposure of compound 1 to cell line 1 under each of conditions 1 to F. Accordingly, in some embodiments, weight 164-(2-1)-1-H is the top correlation within correlations H-1 through H-F.

In some embodiments, a respective weight (e.g., weight 164) is a measure of central tendency of a subset of the correlations 156. In some embodiments, the subset is composed of the best correlations in the set of correlations represented by the weight. For example, in some embodiments, the subset of correlations is the top 2, 3, 4, 5, 6, 7, 8, 9, 10, or more correlations represented by the weight. In some embodiments, the subset of correlations is composed of a certain percentage of the top correlations, e.g., the top 1%, 2%, 3%, 4%, 5%, 6%, 7%, 8%, 9%, 10%, 15%, 20%, 25%, 30%, etc. For example, referring to FIG. 2A, weight 164-(2-1)-1-H represents the correlations (e.g., correlations H-1 through H-F) between (i) the response signature for exposure of compound 2 to cell line 1 under exposure condition H, and (ii) the response signatures for exposure of compound 1 to cell line 1 under each of conditions 1 to F. Accordingly, in some embodiments, weight 164-(2-1)-1-H is a measure of central tendency of the top two correlations within correlations H-1 through H-F.

In some embodiments, the weighting is done at the exposure condition level, such that a weight 164 is generated summarizing a correlation between (i) a response signature for exposure of a first respective compound to a respective cell line under a respective exposure condition, and (ii) the response signatures for exposure of a second respective compound to the respective cell line under each exposure condition (e.g., weights 164 for the comparison of compound 1 to compound 2 in cell line 1, as illustrated in FIG. 2A).

Accordingly, with reference to method 300 in FIGS. 3A-3D, in some embodiments, for a respective pair of compounds in the plurality of compounds (e.g., compounds 1 and 2, as represented in FIG. 2A), the one or more weights 160 for the respective pair of compounds (e.g., weight set 262-(1-2)-1 to 262-(1-2)-A as illustrated in FIGS. 2A and 2B) includes a plurality of weights 160 (e.g., weights 164 as illustrated in FIGS. 2A and 2B), each respective weight 164 in the plurality of weights 160 corresponding to a comparison between (i) a respective response signature 146 corresponding to exposure of a first respective compound in the respective pair of compounds to a respective cell line in the plurality of cell lines under a respective exposure condition in the plurality of exposure conditions, and (ii) the set of response signatures 144 corresponding to exposure of the second respective compound in the respective pair of compounds to the respective cell line under a respective exposure condition 146 in the plurality of exposure conditions.

In some embodiments, the plurality of weights 160 for the comparison of a respective pair of compounds in the plurality of compounds (e.g., weight sets 262 for the comparison of compound 1 with compound 2, as illustrated in FIG. 2B) are further pruned to form a sparse set of weights (e.g., sparse weight sets 166 for the comparison of compound 1 with compound 2, as illustrated in FIG. 2B), e.g., to remove weights corresponding to comparisons between exposure conditions that don't represent biologically-relevant conditions for one or both of the compounds in the compound pair. In some embodiments, each weight in the plurality of weights is compared to respective threshold, e.g., requiring a minimal level of correlation, and only weights meeting the threshold are used to form the sparse weight sets.

In some embodiments, the weighting is done at the cell line level, such that a weight 164 is generated summarizing a correlation between (i) the response signatures for exposure of a first respective compound to a respective cell line under each exposure condition, and (ii) the response signatures for exposure of a second respective compound to the respective cell line under each exposure condition (e.g., referring to FIG. 2A, a single weight would represent each of correlations 1-1 through H-F).

Cluster Formation

Having generated one or more weights 160 (e.g., weight sets 262 for the comparison of compound 1 to compound 2 across cell lines 1 to A, as illustrated in FIG. 2B) summarizing individual measures of correlation 156 for pairwise comparisons of response signatures 146 obtained following exposure of different compounds to different cell lines under different exposure conditions, clusters of compounds 172 are then formed based on the summary weights 160, identifying groups of compounds that have similar response signatures across a range of cell types, as represented by high correlations. For example, as illustrated in FIG. 2C, compound cluster 272-2 is formed, containing compounds i, j, and k, having the greatest correlations in response signatures with compound 2 across cell lines 1 to A, as determined by evaluating comparison scores 268 summarizing weights 164 with a threshold 280).

Accordingly, with reference to method 300 in FIGS. 3A-3D, the method includes forming a plurality of compound clusters 170, each respective compound cluster 172 representing a respective compound 174 (e.g., compound cluster 272-2 in FIG. 2C represents compound 2, because the comparison scores used to determine the cluster represent correlations between response signatures for each of the other compounds relative to response signatures for compound 2) in the plurality of compounds and including a corresponding subset of compounds in the plurality of compounds, where each respective compound in the corresponding subset of compounds satisfies one or more weight criteria 132 with respect to respective compound.

In some embodiments, the one or more weight criteria 132 includes (328) a requirement that the respective pair of compounds in the corresponding unique subset of compounds have a correlation value (e.g., comparison score 168 as illustrated in FIG. 1D and/or comparison score 268 as illustrated in FIG. 2C) across all or a subset of the plurality of cell lines that is within a threshold percent (e.g., threshold 280 as illustrated in FIG. 2C) of an upper correlation bound identified for the plurality of compounds across the plurality of cell lines. In some embodiments, the threshold percent is between five percent and fifty percent (330). In some embodiments, the threshold percent is five, ten, fifteen, twenty, twenty-five, thirty, thirty-five, forty, forty-five, or fifty percent. In some embodiments, the threshold percent is no more than five, ten, fifteen, twenty, twenty-five, thirty, thirty-five, forty, forty-five, or fifty percent.

In some embodiments, the correlation value (e.g., comparison score 168 as illustrated in FIG. 1D and/or comparison score 268 as illustrated in FIG. 2C) is a summary statistic representing the weights 164 (e.g., weight sets 262 or sparse weight sets 266 for the comparison of compound 1 with compound 2, as illustrated in FIG. 2B) determined for the comparison of a respective pair of compounds in the plurality of compounds.

In some embodiments, the correlation value (e.g., comparison score 168 as illustrated in FIG. 1D and/or comparison score 268 as illustrated in FIG. 2C) is a measure of central tendency of the individual weights 164 determined for the comparison between the respective pair of compounds. In some embodiments, the measure of central tendency is an arithmetic mean, weighted mean, midrange, midhinge, trimean, geometric mean, geometric median, Winsorized mean, median, or mode of the distribution of weights 164. In some embodiments, the correlation value is a mean of the weights 164 determined for the comparison between the respective pair of compounds.

In some embodiments, the correlation value (e.g., comparison score 168 as illustrated in FIG. 1D and/or comparison score 268 as illustrated in FIG. 2C) is greatest weight within the set of weights 164 determined for the comparison between the respective pair of compounds. For example, referring to FIG. 2C, comparison score 268-(1-2) represents the correlation value for the comparison of compounds 1 and 2 across all cell lines, as represented by weights 266 in matrix 267-(1-2). In some embodiments, comparison score 268-(1-2) is the largest weight 266 in matrix 267.

In some embodiments, the correlation value (e.g., comparison score 168 as illustrated in FIG. 1D and/or comparison score 268 as illustrated in FIG. 2C) is a measure of central tendency of a subset of the weights 164 determined for the comparison between the respective pair of compounds. In some embodiments, the subset is composed of the largest weights 164 determined for the comparison between the respective pair of compounds. For example, in some embodiments, the subset of weights is the top 2, 3, 4, 5, 6, 7, 8, 9, 10, or more weights 164 determined for the comparison between the respective pair of compounds. In some embodiments, the subset of weights is composed of a certain percentage of the top weights, e.g., the top 1%, 2%, 3%, 4%, 5%, 6%, 7%, 8%, 9%, 10%, 15%, 20%, 25%, 30%, etc.

In some embodiments, the one or more weight criteria 132 is a plurality of weight criteria and the plurality of weight criteria further includes a requirement that the subset of the plurality of cells lines be at least five different cell lines (332). In some embodiments, the one or more weight criteria is a plurality of weight criteria and the plurality of weight criteria further includes a requirement that the subset of the plurality of cells lines be at least 3, 4, 5, 6, 7, 8, 9, 10, 11, 12, 13, 14, 15, 16, 17, 18, 19, or 20 different cell lines.

In other embodiments, any one of a number of clustering techniques can be used, examples of which include, but are not limited to, hierarchical clustering, k-means clustering, and density based clustering. In one specific embodiment, a hierarchical density based clustering algorithm is used (referred to as HDBSCAN, Campello, R. J., Moulavi, D., Zimek, A., & Sander, J. (2015), "Hierarchical density estimates for data clustering, visualization, and outlier detection," *ACM Transactions on Knowledge Discovery from*

Data (*TKDD*), 10(1), 5) which is hereby incorporated by reference. In another embodiment, a community detection based cluster algorithm is used, such as Louvain clustering (Blondel, V. D., Guillaume, J. L., Lambiotte, R., & Lefebvre, E. (2008), "Fast unfolding of communities in large networks" *Journal of statistical mechanics: theory and experiment*, 2008(10), P10008), which is hereby incorporated by reference.

In some embodiments, as discussed above, each compound in the plurality of compounds does not have to be tested against the same plurality of cell lines. Rather, this criteria is designed to identify string correlations between response signatures caused by compounds across a range of different cell types. For example, referring to FIG. 2C, response signatures 146 were evaluated, relative to response signatures for compound 2, for each of compounds i through n in a plurality of the same cell lines that were used to evaluate compound 2, e.g., at least 5 cell lines. However, the at least 5 cell lines in which compound i was evaluated against does not have to be the same at least 5 cell lines in which compound j was evaluated against. Rather, it is just that compound i and compound 2 were evaluated in at least 5 of the same cell lines and compound j and compound 2 were evaluated in at least 5 of the same cell lines, which may be the same 5 cell lines or a different 5 cell lines.

In some embodiments, a respective compound cluster 172 is formed representing each compound in the plurality of compounds. For example, referring to a data set 140 containing response signature data for each of compounds 1 through B, as illustrated in FIG. 1B, B compound clusters 172 would be formed for the B compounds in the compound set. However, in other embodiments, a respective compound cluster 172 is formed for a subset of the compounds in the plurality of compounds. For instance, referring to the plurality of compound clusters 170 illustrated in FIG. 1E, D compound clusters, representing less than B compounds, are formed for the plurality of B compounds for which response signatures 146 were analyzed.

In some embodiments, the method includes forming at least 5 compound clusters, representing at least 5 respective compounds in the plurality of compounds. In some embodiments, the method includes forming at least 10 compound clusters, representing at least 10 respective compounds in the plurality of compounds. In some embodiments, the method includes forming at least 25 compound clusters, representing at least 25 respective compounds in the plurality of compounds. In some embodiments, the method includes forming at least 50 compound clusters, representing at least 50 respective compounds in the plurality of compounds. In some embodiments, the method includes forming at least 100 compound clusters, representing at least 100 respective compounds in the plurality of compounds. In some embodiments, the method includes forming at least 500 compound clusters, representing at least 500 respective compounds in the plurality of compounds. In some embodiments, the method includes forming at least 1000 compound clusters, representing at least 1000 respective compounds in the plurality of compounds. In some embodiments, the method includes forming at least 5000 compound clusters, representing at least 5000 respective compounds in the plurality of compounds. In some embodiments, the method includes forming at least 10,000 compound clusters, representing at least 10,000 respective compounds in the plurality of compounds. In some embodiments, the method includes forming at least 50,000 compound clusters, representing at least 50,000 respective compounds in the plurality of compounds. In some embodiments, the method includes forming at least 100,000 compound clusters, representing at least 100,000 respective compounds in the plurality of compounds. In some embodiments, the method includes forming at least 500,000 compound clusters, representing at least 500,000 respective compounds in the plurality of compounds. In some embodiments, the method includes forming at least 1,000,000 compound clusters, representing at least 1,000,000 respective compounds in the plurality of compounds.

Identifying Compound Properties

Having formed one or more compound clusters, e.g., a plurality of compound cluster, the compound clusters can be used to identify previously unknown properties for one or more compounds based on co-clustering of the compound with one or more other compounds in one or more clusters. For instance, when several compounds in a cluster have previously been identified as having a particular function (e.g., protease inhibition), there is a high probability that a previously unannotated compound in that same cluster also has that same function (e.g., is also a protease inhibitor). Accordingly, with reference to method 300 in FIGS. 3A-3D, in some embodiments, the method also includes identifying (338) the compound property of the test compound from one or more properties of one or more compounds in one or more compound clusters 172 in the plurality of compound clusters 170 that contain the test compound. In some embodiments, one or more compound clusters 172 in the plurality of compound clusters 170 that contain the test compound In some embodiments, the method further includes using (344) the compound property of the test compound and the one or more properties of the one or more compounds in the one or more compound clusters in the plurality of compound clusters that contain the test compound to identify a molecular target for a disease indication. For example, for a test compound known to cause an effect for a particular disease indication, without prior knowledge of the molecular target(s) through which the test compound acts, the method includes identifying one or more compounds, which known molecular targets, in one or more compound clusters in the plurality of compound clusters that also include the test compound, to identify a molecular target of the test compound.

In some embodiments, the method further includes using (346) the compound property of the test compound and the one or more properties of the one or more compounds in the one or more compound clusters in the plurality of compound clusters that contain the test compound to repurpose the test compound. For example, for a test compound that is a drug for a first disease indication, in some embodiments, the method includes identifying one or more compounds used to treat a second disease indication in one or more compound clusters in the plurality of compound clusters that also include the test compound, to repurpose the drug for use in treating the second disease indication.

In some embodiments, the compound property of the test compound is determined from one or more properties of one or more compounds in the compound cluster in the plurality of compound clusters associated with the test compound though pharmacophore analysis (340). In some embodiments, the method includes identifying a pharmacophore based on analysis of a plurality of compounds clustering within one or more respective clusters in the plurality of clusters. For example, in some embodiments, compounds that cluster into at least 2, at least 3, at least 4, at least 5, at least 6, at least 7, at least 8, at least 9, at least 10, or more of the same clusters in the plurality of clusters are used to identify a pharmacophore. Methods for pharmacophore analysis are known in the art, for example using algorithms such as Catalyst, Unity, LigandScout, Phase, Pharao, MOE, Pharmer, and/or POT. For a review and comparative analysis of these pharmacophore algorithms see, for example, Sanders et al., J. Chem. Inf. Model., 52(6), 1607-20 (2012), which is incorporated herein by reference, in its entirety, for all purposes.

In some embodiments, the compound property of the test compound is a mechanism-of-action annotation (342). For instance, in some embodiments, identification of a second compound in one or more compound clusters that also contain the test compound can be used to infer that the test compound shares a mechanism of action with the second compound, thereby identifying that mechanism of action for the test compound. In some embodiments, computation inference methods can be used to identify a mechanism of action based on compounds that cluster into at least 2, at least 3, at least 4, at least 5, at least 6, at least 7, at least 8, at least 9, at least 10, or more of the same clusters in the plurality of clusters that also contain the test compound. Methods for computation inference of mechanisms of action are known in the art. See, for example, Feng et al., "Multi-parameter phenotypic profiling: using cellular effects to characterize small-molecule compounds," Nat Rev Drug Discov., 8(7):567-78 (2009), and Wagner and Clemons, "Connecting synthetic chemistry decisions to cell and genome biology using small-molecule phenotypic profiling," Curr Opin Chem Biol, 13(5-6):539-48 (2009), which are incorporated herein by reference, in their entireties, for all purposes.

EXAMPLES

Example 1—Library of Integrated Network-Based Cellular Signatures (LINCS) Data

The Library of Integrated Network-Based Cellular Signatures (LINCS) consortium archives datasets consisting of assay results from cultured and primary human cells treated with perturbagens, e.g., bioactive small molecules, ligands such as growth factors and cytokines, or genetic perturbations. The LINCS consortium archives include data sets from many different types of assays used to monitor cell responses, providing data on transcriptional responses, protein expression responses, cell phenotypic responses measured, e.g., by biochemical and/or cellular imaging assays. In many cases, assays are performed across multiple cell lines, under multiple environmental conditions, and/or using multiple perturbagen concentrations. Accordingly, the LINCS consortium includes large-scale data on perturbation-induced molecular and cellular signatures. More information on the LINCS consortium can be found online at the URL lincsproject.org.

Example 2—Demonstration of Compound Clustering to Enrich for Molecules Having Common Mechanisms of Action A method of associating a test compound with a compound property, where the test compound is in a plurality of compounds is provided in this example. The method comprises (e.g., at a computer system comprising a memory and one or more processors), obtaining one or more datasets in electronic form. The one or more datasets comprises or collectively comprises, for each respective cell line in a plurality of cell lines (where the plurality of cell lines comprises five or more cell lines) for each respective compound in the plurality of compounds, for each respective exposure condition in a plurality of exposure conditions for the respective compound, a corresponding response signature for the respective compound in the respective cell line under the respective exposure condition.

In this example, the one or more datasets is L1000, a high-throughput gene expression assay that measures the mRNA transcript abundance of 978 genes and 80 control transcripts, chosen for their invariant expression across cell states, from human cells. This multiplexed gene expression assay uses ligation mediated amplification (LMA) of RNA sequence specific probes combined with Luminex based detection to generate the expression profiles of the 978 genes per sample in a 384 well format. Details about the assay protocol are described in Davis et al., "L1000 SOP", published by the Broad Institute, pp. 1-11 (Updated Dec. 20, 2016) and Subramanian et al., Cell, 171(6):1437-52 (2017), the contents of which are hereby incorporated by reference, in their entireties, for all purposes.

In this example, the plurality of cell lines is the plurality of cell lines represented in the LINCS L1000 database available on the Internet at lincs.hms.harvard.edu/db/cells/as set forth in Table 3 below. Each of these cells lines is human.

TABLE 3

Plurality of cell lines represented in LINCS L1000 Database.

| NAME | LINCS ID | ORGAN | CELL TYPE |
| --- | --- | --- | --- |
| 5637 | LCL-1702 | urinary bladder | epithelial |
| 647-V | LCL-1708 | urinary bladder | epithelial-like |
| A375.S2 | LCL-1231 | skin | epithelial |
| AGS | LCL-1893 | stomach | epithelial |
| BPH-1 | LCL-2095 | prostate | epithelioid |
| Ca Ski | LCL-1541 | cervix | epithelial |
| Ca9-22 | LCL-2033 | head & neck | epithelial-like |
| CAL-51 | LCL-1472 | breast | epithelial-like |
| Calu-1 | LCL-1580 | lung | epithelial |
| Calu-3 | LCL-1631 | lung | epithelial |
| COLO-679 | LCL-1232 | skin | fibroblastic |
| COLO-800 | LCL-1233 | skin | epithelial-like |
| FU97 | LCL-1894 | stomach | epithelial-like |
| HEC-1 | LCL-1496 | uterus | |
| HLF | LCL-1938 | liver | |
| HUTU-80 | LCL-1150 | intestine | epithelial |
| IA-LM | LCL-1778 | lung | |
| Ishikawa | LCL-1497 | uterus | epithelial-like |
| Ishikawa (Heraklio) 02 ER- | LCL-1498 | uterus | epithelial |
| IST-MEL1 | LCL-1234 | skin | epithelial-like |
| JHH-6 | LCL-1923 | liver | epithelial-like |
| KATO III | LCL-2003 | stomach | spherical |
| KMRC-20 | LCL-1755 | kidney | epithelial-like |
| KYSE-140 | LCL-1547 | esophagus | |
| KYSE-150 | LCL-1548 | esophagus | epithelioid |
| KYSE-180 | LCL-1549 | esophagus | epithelioid |
| KYSE-450 | LCL-1550 | esophagus | epithelioid |
| LNZTA3WT4 | LCL-1345 | brain | |
| MCF7 | LCL-1460 | breast | epithelial |
| MDA-MB-435S | LCL-1307 | skin | melanocyte |
| MT-3 | LCL-1473 | breast | epithelial |
| NCI-H1648 | LCL-1632 | lung | |
| NCI-H1651 | LCL-1633 | lung | epithelial |
| NCI-H1703 | LCL-1582 | lung | epithelial |
| NCI-H1915 | LCL-1598 | lung | large cell |
| NCI-H2023 | LCL-1599 | lung | |
| NCI-H810 | LCL-1670 | lung | epithelial |
| PC-9 | LCL-1630 | lung | |
| PE/CA-PJ15 | LCL-1212 | head & neck | epithelial-like |
| PL4 | LCL-1098 | pancreas | |
| SJCRH30 | LCL-1408 | muscle | fibroblast |
| SK-LMS-1 | LCL-1286 | uterus | |
| SK-MES | LCL-1583 | lung | epithelial |
| SK-OV-3 | LCL-1517 | ovary | epithelial |
| SNB75 | LCL-1346 | brain | |
| SW527 | LCL-1474 | breast | epithelial |

TABLE 3-continued

Plurality of cell lines represented in LINCS L1000 Database.

| NAME | LINCS ID | ORGAN | CELL TYPE |
|---|---|---|---|
| SW620 | LCL-1157 | intestine | epithelial |
| T24 | LCL-1709 | urinary bladder | epithelial |
| WiDr | LCL-1169 | intestine | epithelial |
| HME1 | LCL-2083 | breast | epithelial |
| SK-BR-3 | LCL-1475 | breast | epithelial |
| MDA-MB-231 | LCL-1461 | breast | epithelial |
| A-375 | LCL-1235 | skin | epithelial |
| HeLa | LCL-1512 | cervix | epithelial |
| A549 | LCL-1601 | lung | |
| AU565 | LCL-1462 | breast | |
| BT-20 | LCL-1476 | breast | |
| BT-474 | LCL-1308 | breast | |
| BT-483 | LCL-1309 | breast | |
| BT-549 | LCL-1310 | breast | |
| C32 | LCL-1238 | skin | |
| CAMA-1 | LCL-1466 | breast | |
| COLO 858 | LCL-1242 | skin | |
| HCC1143 | LCL-1329 | breast | |
| HCC1395 | LCL-1330 | breast | |
| HCC1419 | LCL-1314 | breast | |
| HCC1428 | LCL-1467 | breast | |
| HCC1569 | LCL-1480 | breast | |
| HCC1806 | LCL-1960 | breast | |
| HCC1937 | LCL-1331 | breast | |
| HCC1954 | LCL-1332 | breast | |
| HCC202 | LCL-1333 | breast | |
| HCC38 | LCL-1334 | breast | |
| HCC70 | LCL-1335 | breast | |
| Hs 578T | LCL-1315 | breast | |
| MB 157 | LCL-1484 | breast | |
| MDA-MB-134-VI | LCL-1316 | breast | |
| MDA-MB-157 | LCL-1916 | breast | |
| MDA-MB-175-VII | LCL-1317 | breast | |
| MDA-MB-361 | LCL-1468 | breast | |
| MDA-MB-415 | LCL-1469 | breast | |
| MDA-MB-436 | LCL-1470 | breast | |
| MDA-MB-453 | LCL-1485 | breast | |
| MDA-MB-468 | LCL-1471 | breast | |
| PC-3 | LCL-1299 | prostate | |
| RVH-421 | LCL-1255 | skin | |
| T47D | LCL-1486 | breast | |
| UACC-812 | LCL-1319 | breast | |
| UACC-893 | LCL-1320 | breast | |
| WM-115 | LCL-1260 | skin | |
| WM1552C | LCL-1261 | skin | |
| ZR-75-1 | LCL-1321 | breast | |
| ZR-75-30 | LCL-1322 | breast | |
| 184B5 | LCL-2081 | breast | epithelial |
| DU4475 | LCL-1323 | breast | epithelial |
| HCC1187 | LCL-1324 | breast | epithelial |
| HCC1500 | LCL-1325 | breast | epithelial |
| HCC1599 | LCL-1326 | breast | epithelial |
| HCC2157 | LCL-1327 | breast | epithelial |
| HCC2218 | LCL-1328 | breast | epithelial |
| MCF 10A | LCL-2085 | breast | epithelial |
| MCF 10F | LCL-2102 | breast | epithelial |
| Ramos (RA 1) | LCL-1097 | blood | |
| THP-1 | LCL-1072 | blood | |
| U-87 MG | LCL-1364 | brain | |
| U-937 | LCL-1125 | lymphatic system | |
| LOXIMVI | LCL-1276 | skin | |
| MMAC-SF | LCL-1277 | skin | |
| MZ7-mel | LCL-1279 | skin | |
| SUM1315MO2 | LCL-2066 | breast | |
| SUM149PT | LCL-2067 | breast | |
| SUM159PT | LCL-2068 | breast | |
| SUM185PE | LCL-2069 | breast | |
| SUM225CWN | LCL-2070 | breast | |
| SUM229PE | LCL-2065 | breast | |
| SUM52PE | LCL-2071 | breast | |
| 184A1 | LCL-2080 | breast | |
| MCF12A | LCL-2082 | breast | |
| MX1 | LCL-2072 | breast | |
| T47DKBLUC | LCL-2064 | breast | |
| 600MPE | LCL-2073 | breast | |
| HCC2185 | LCL-2074 | breast | |
| HCC3153 | LCL-2075 | breast | |
| LY2 | LCL-2076 | breast | |
| ZR75B | LCL-2077 | breast | |
| BCWM.1 | LCL-2094 | blood | |
| MWCL.1 | | blood | |
| NGP | LCL-2103 | nervous system | |
| K2 | LCL-2091 | skin | |
| SKMEL28 | LCL-2092 | skin | |
| HeLa ICRP | LCL-2096 | cervix | epithelial |
| HeLa ICRP FLIP-L-mCherry | LCL-2099 | cervix | epithelial |
| HeLa ICRP FLIP-S-mCherry | LCL-2100 | cervix | epithelial |
| HeLa ICRP Bcl-2-mCherry | LCL-2097 | cervix | epithelial |
| HeLa ICRP Bcl-XL-mCherry | LCL-2098 | cervix | epithelial |
| 21MT-1 | | breast | epithelial |
| 21NT | | breast | epithelial |
| 21PT | | breast | epithelial |
| CAL-120 | | breast | |
| CAL-148 | | breast | epithelioid |
| CAL-85-1 | | breast | epithelial |
| EFM-19 | | breast | epithelioid |
| EFM-192A | | breast | epithelioid |
| EFM-192B | | breast | epithelioid |
| EFM-192C | | breast | epithelioid |
| HBL-100 | | breast | epithelial |
| JIMT-1 | | breast | epithelial |
| HMT-3522 S1 | | breast | epithelial |
| SUM102PT | | breast | |
| SUM190PT | | breast | |
| SUM44PE | | breast | |
| HMT-3522 T4-2 | | breast | epithelial |
| MCF 10A-H2B-mCherry | | breast | epithelial |
| 184A1 F3aN400-Venus NLS-mCherry | | breast | |
| MCF 10A F3aN400-Venus-P2A-NLS-mCherry | | breast | epithelial |
| MCF 10A F3aN400S294A/S344A-Venus-P2A-NLS-mCherry | | breast | epithelial |
| MCF 10A F3aN400T32A/S253A/S315A-Venus-P2A-NLS-mCherry | | breast | epithelial |
| 184A1 F3aN400-Venus-P2A-NLS-mCherry | | breast | |
| 184A1 F3aN400S294A/S344A-Venus-P2A-NLS-mCherry | | breast | |
| 184A1 F3aN400T32A/S253A/S315A-Venus-P2A-NLS-mCherry | | breast | |
| MCF 10A EKAREV-P2A-F3aN400-mCherry | | breast | epithelial |
| MCF 10A EKAREV H2B-mCherry | | breast | epithelial |
| PDX1258 | | breast | epithelial |
| PDX1328 | | breast | epithelial |
| PDXHCI002 | | breast | epithelial |
| PDX1206 | | breast | epithelial |
| EVSA-T | | breast | epithelial |
| MDAMB330 | | breast | epithelial |
| MGH312 | | breast | epithelial |
| MGH358 | | breast | epithelial |

In this example, the plurality of compounds is 18,000 perturbagens downloaded from the LINCS consortium archives in AnnData format. Specifically, LINCS L1000 Level 4 data on over 18,000 perturbagens was downloaded from the LINCS consortium archives as an AnnData format. Level 4 data contain z-scores for each gene with all expression values of that gene on a plate as the background. z-Scores indicate the levels at which genes are differentially expressed.

In this example, the plurality of exposure conditions for each respective compound includes different concentrations of the respective compound that a respective cell line was incubated against as well as different time periods for this incubation. For instance, one hypothetical exposure condition is incubation of cell line A against compound W at a concentration of 0.3 µM for 1 hour, another hypothetical exposure condition is incubation of cell line A against compound W at a concentration of 0.5 µM for 1 hour, and yet another hypothetical exposure condition is incubation of cell line A against compound W at a concentration of 0.3 µM for 2 hours.

In this example, a corresponding response signature for a respective compound in a respective cell line under a respective exposure condition is the mRNA transcript abundance of the 978 genes and 80 control transcripts referenced above. Thus, each cell line is exposed to a given compound under given exposure conditions and then the corresponding response signature, in the form of the mRNA transcript abundance of the 978 genes and 80 control transcripts referenced above, is measured. As such, the corresponding response signature comprises a corresponding plurality of quantitative biomarker measurements (in this example mRNA abundance) for the respective cell line across a plurality of biomarkers (in this example mRNA transcript abundance for the 978 genes and 80 control transcripts) upon exposure of the respective cell line to the respective compound at the respective exposure condition (e.g., specific concentration and incubation time), where the plurality of biomarkers comprises one hundred or more biomarkers (e.g., mRNA for 978 different genes).

In the example, for each respective cell line in the plurality of cell lines, for each respective pair of compounds in the plurality of compounds, a determination is made, for each unique combination of respective exposure conditions for the respective pair of compounds, of a corresponding correlation of the corresponding plurality of quantitative biomarker measurements for the respective pair of compounds across the plurality of biomarkers, thereby determining one or more correlation values for the respective pair of compounds. In particular, compounds were subsetted for each cell type, perturbation time, and Pearson correlations were calculated between each pair of molecules. Because perturbagens were tested against cell lines multiple time under different conditions, e.g., at different doses, different exposure times, different chemical environments, etc., an n×m matrix of correlations is generated (e.g., matrix 254-(1-2)-1 as illustrated in FIG. 2A, which is an H×F matrix representing the H conditions compound 2 was tested under in cell line 1 and the F conditions compound 2 was tested under in cell line 1).

Further in this example, one or more weights for each respective pair of compounds was determined from the one or more correlations values for each respective pair of compounds. In this example, a weight for the correlation between each compound was calculated for each experiment/condition under which a compound was tested by summing up the row of Pearson correlations corresponding to the experiment/condition. For example, as illustrated in FIG. 2A, Weight$_{1-1}$ corresponds to a summary statistic for the row of correlations for exposure condition 2 of compound 2 (Correlations$_{1-1}$ to Correlations$_{1-F}$) against compound 1. A given weight was set to zero if the row-sum correlation score that the given weight represents was negative. Thus, referring to FIG. 2A, if the row-sum correlation of the first row was negative (row-sum correlation for correlations 1-1 through 1-F), weight 1-1 was set to zero.

Next, in this example, the weights calculated for each pair of compounds, for each cell line, were collated into a single representation. For example, as illustrated in FIG. 2B, weight set 1, labeled weight set 262-(1-2)-1 in FIG. 2B, is a single representation that includes all the weights calculated for the comparison between compound 1 and compound 2 in cell line 1. As further illustrated in FIG. 2B, weight set 2, labeled weight set 262-(1-2)-2 in FIG. 2B, is a single representation that includes all the weights calculated for the comparison between compound 1 and compound 2 in cell line 2, and so forth. A threshold was applied to sparsify each single representation (each the collated correlation matrix). That is, elements of a single representation that did not satisfy the threshold were dropped from the single representation. For instance, referring to labeled weight set 262-(1-2)-1, each component weight in labeled weight set 262-(1-2)-1 that did not satisfy the threshold were dropped from the single representation. Those weights that remained form sparse weight set 1, labeled 266-(1-2)-1 in FIG. 2B. As an example, consider the case where the threshold if 0.4. In this instance, each weight in labeled weight set 262-(1-2)-1 that does not exceed 0.4 is dropped from labeled weight set 262-(1-2)-1 in order to form the corresponding sparse weight set 1, labeled 266-(1-2)-1 in FIG. 2B.

Repeating this procedure for each cell line, for each unique pair of compounds in the plurality of compounds gives a compendium of cell type-dependent similarities. For example, as illustrated in FIG. 2B, each of weight sets 262-(1-2)-1 to 262-(1-2)-A were sparsified, such that resulting sparse weight sets 266-(1-2)-1 to 266-(1-2)-A had fewer weights than in weight sets 262-(1-2)-1 through 262-(1-2)-A. Then, for each pair of compounds, the similarity matrices were collated across the cell types. For instance, as illustrated in FIG. 2C, sparse weight sets 266-(1-2)-1 to 266-(1-2)-A were collated into matrix 267-(1-2) representing the correlation between compounds 1 and 2 across all of cell lines 1 to A.

In this example, pairs of compounds were filtered out if they were co-experimented in less than five different cell types. However, data could have been preselected to only include pairs of combinations tested across at least five different cell types.

As illustrated in FIG. 2C, a single comparison score 268-(1-2) between compound 1 and compound 2 can be formed from the sparse weight sets for each cell line. That is, referring to data structure 267-(1-2) each row can be considered a vector and a correlation coefficient can be calculated across the resulting vectors to form comparison score 268-(1-2). This comparison score provides a score for how well the response signatures of compounds 1 and 2 correlate with each other across the cell lines. In this way, each unique pair of compounds in the plurality of compounds is assigned a comparison score. These comparison scores can be used to cluster the compounds into compound clusters, termed cliques. For instance, in one approach, a plurality of compound clusters is formed, where each respective compound cluster represents a different compound in the plurality of compounds and comprises a corresponding subset of compounds in the plurality of compounds, where each respective compound in the corresponding subset of compounds satisfies one or more weight criteria with respect to the different compound. This is illustrated in FIG. 2C. Here the "different compound" is compound 2, and compounds i, j, and k each have a comparison score with compound 2 that satisfies threshold 280 and thus compounds 2, i, j, and k are in a compound clique. That is, the comparison score for the compound pair 2, i, the comparison score for the compound pair 2, j, and the comparison score for the compound pair 2, k each satisfy threshold 280. Consider the case where the threshold 280 is 0.4. In this instance, that would mean that the comparison score for the compound pair 2, i, the comparison score for the compound pair 2, j, and the comparison score for the compound pair 2, k are each greater than 0.4. In FIG. 2C, compound 1 fails to satisfy the threshold 280, meaning that the comparison score for the compound pair 2, 1 is less than 0.4 (taking the example threshold 280 as 0.4).

Compound clusters were then defined, on a particular compound by particular compound basis, by selecting those compounds having a measure of similarity with the particular compound that is within 30% of the measure of similarity for the compound having the highest measure of similarity with the particular compound. For example, as illustrated in FIG. 2C, sparse weight matrices 267 for the comparison of each other compound with compound 2 are used to generate a comparison score 268. These comparison scores are ranked in FIG. 2C, and a threshold 280 is set at 70% of the highest comparison score 268-(i–2). The resulting compound cluster includes compound 2 and compounds i, j, and k because they each have a comparison score, relative to compound 2, above threshold 280.

Figure 5:
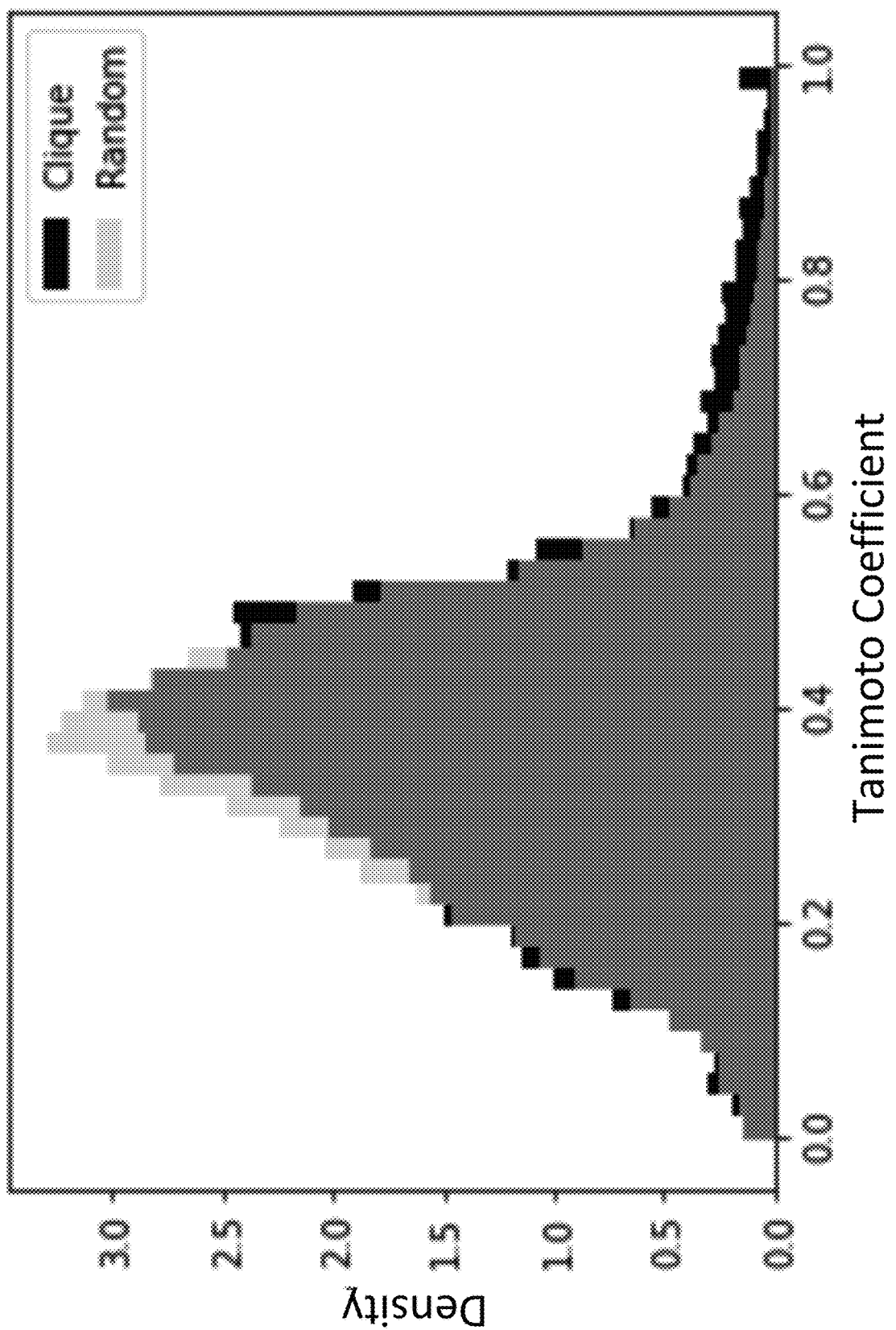
FIG. 5 illustrates analysis of chemical similarity among perturbagens in a compound cluster elucidated using the methods described herein, in accordance with various embodiments of the present disclosure, and chemical similarity among random perturbagens.

Example 3—Global Characterization of Compound Clusters Shows Enrichment of Related Compounds Several approaches were taken to analyze whether the compound clusters identified in Example 3 were enriched for perturbagens (e.g., chemical compositions) sharing biological effects. First, molecules that target a particular protein often share a molecular substructure, as such, groupings of biologically-related perturbagens should have higher Tanimoto coefficients (a measure of structural similarity) than groupings of random perturbagens. To test if the compound clusters were enriched for molecular structure similarity, a Tanimoto coefficient was determined for each cluster, as well as for a random grouping of perturbagens corresponding to each compound cluster that has the same number of compounds as the corresponding compound cluster. The coefficients were then plotted as a function of frequency. As shown in FIG. 5, the distribution of Tanimoto coefficients for the compound clusters was shifted higher, relative to the distribution of Tanimoto coefficients for the randomly assigned groupings ($p<0.001$). Accordingly, the compound clustering methods described herein enrich for compounds having structural similarity. For more details on use of the Tanimoto coefficient see, for example, Bero et al., "Weighted Tanimoto Coefficient for 3D Molecule Structure Similarity Measurement," Ithaca, NY: Cornell University Library; 10 (2018), arXiv:1806.05237, the content of which is hereby incorporated by reference in its entirety for all purposes.

Figure 6:
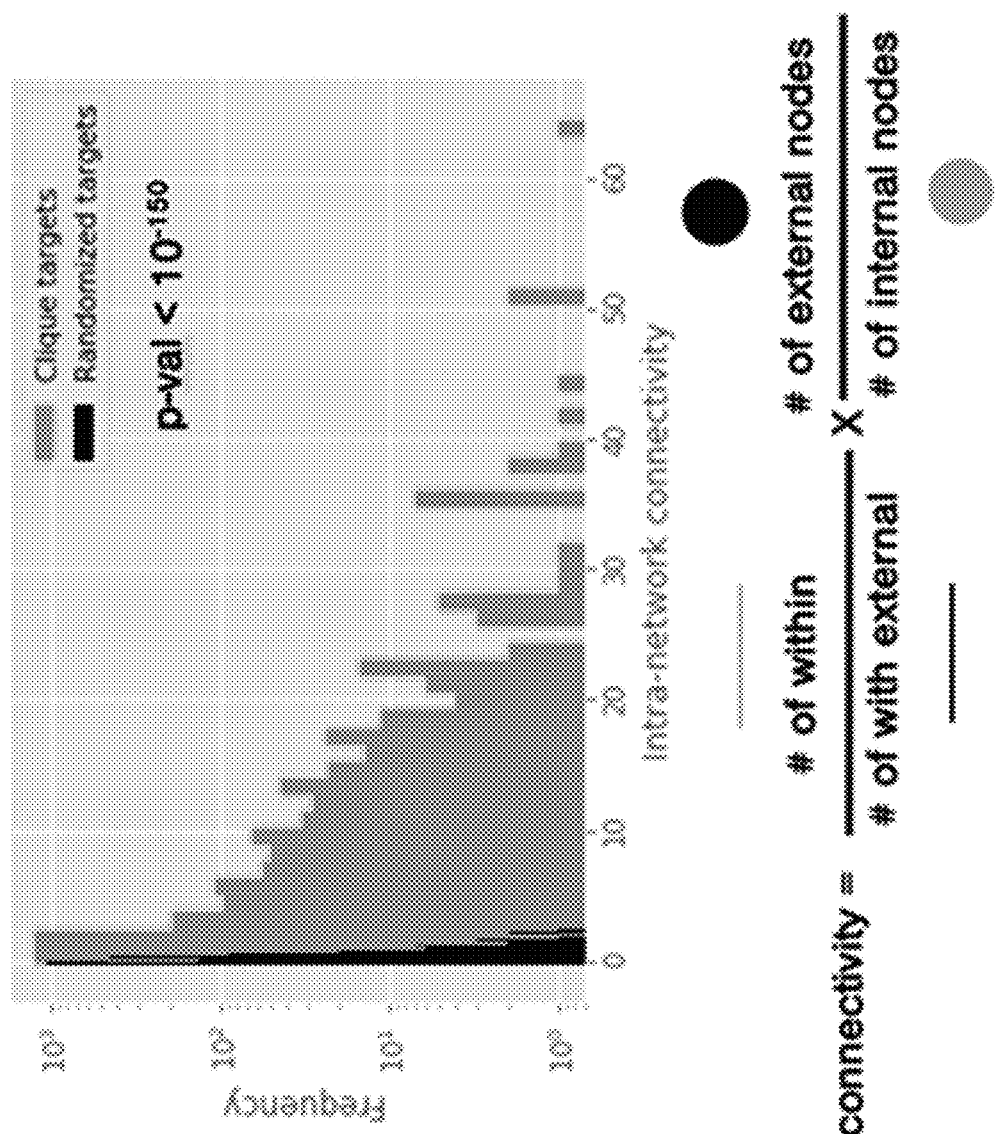
FIG. 6 illustrates an analysis of interaction enrichment provided by methods for associating a test compound with a compound property, in accordance with various embodiments of the present disclosure.
Figure 6:
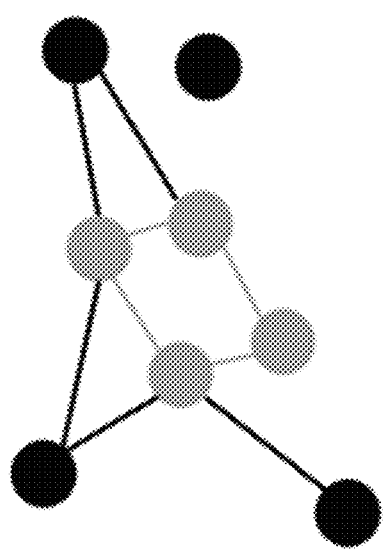

Next, it was determined whether there was an enrichment in the interconnectivity of protein targets reported for the perturbagens in compound clusters, relative to the interconnectivity of protein targets reported for random groupings of perturbagens. To do so, protein-protein interactions within the Protein-Protein Interaction Network from STRINGDB were queried with the reported protein targets for each compound cluster, as well as for reported protein targets for random groupings of perturbagens of the same size as a compound cluster. An interconnectivity score was then calculated according to the metric shown in FIG. 6. The results were then plotted as a function of frequency. As shown in FIG. 6, the intra-network connectivity between perturbagens within compound clusters was significantly higher than the intra-network connectivity between perturbagens within random groupings ($p<0.001$). Accordingly, the compound clustering methods described herein enrich for perturbagens targeting the same molecular pathways.

Example 4—Phenotypic Characterization of a Compound Cluster Formed Around Compound A1

To further investigate whether the perturbagens of a single cluster identified in Example 2 have similar phenotypic responses, a cluster formed around a known compound, referred to herein as Compound A1, a vitamin-D receptor agonist, was investigated. Compound A1 is used to treat hyperparathyroidism (overactive parathyroid glands) and metabolic bone disease in people who have chronic kidney failure. Compound A1 was also discovered to reduce goblet cells, which generate excess mucus in asthma and chronic obstructive pulmonary disease (COPD). The clustering analysis described in Example 2, performed with data on over 18,000 perturbagens, identified a compound cluster of perturbagens around Compound A1.

Figure 7:
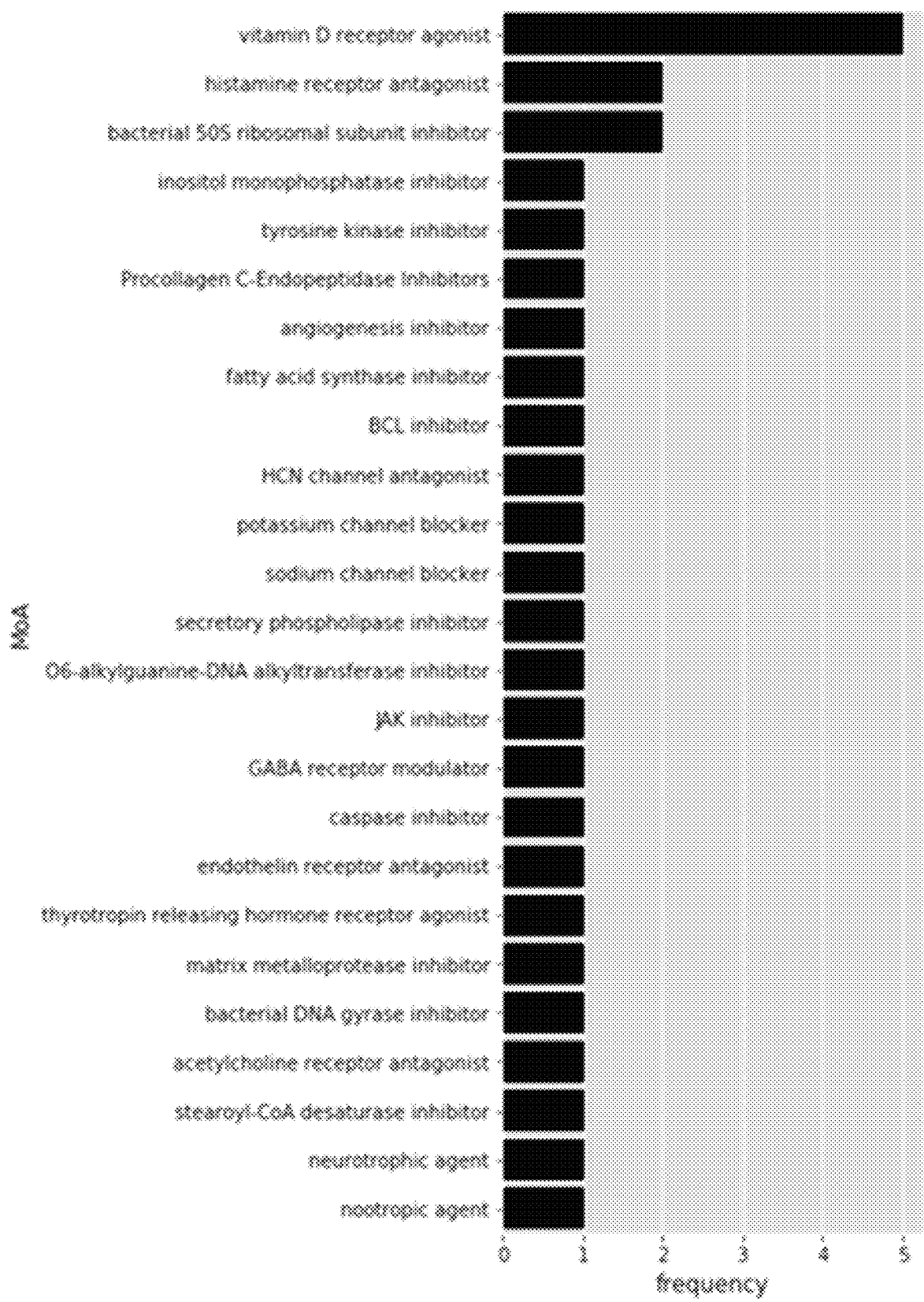
FIG. 7 illustrates characterizations of a compound cluster formed around Compound A1, a vitamin D receptor agonist. Specifically.

Annotated mechanisms of action (MoA) for each member of the identified cluster were evaluated. As illustrated in FIG. 7, the cluster is enriched for Vitamin D receptor agonists, similar to Compound A1. This observation that clique analysis can pick up the vast majority (98%) of vitamin-D receptor agonists from over 18,000 perturbagens is an indication that the clustering analysis works ($p<0.001$). Further, the cluster is also enriched with structural analogs of Compound A1, implying the consistency of the methodology. Finally, the compound cluster included several, structurally-unrelated, compounds, Compound A2, Compound A3, and Compound A4 known to reduce goblet cell hyperplasia and/or inhibit airway remodeling in asthma, as does Compound A1.

Example 5—Phenotypic Characterization of a Compound Cluster Formed Around Compound A5

To further investigate whether the perturbagens of a single cluster identified in Example 2 have similar phenotypic responses, a cluster formed around Compound A5 was investigated. Compound A5 is an mTOR and PI3K inhibitor approved for use as an immunosuppressant for several indications. The clustering analysis described in Example 2, performed with data on over 18,000 perturbagens, identified a compound cluster of perturbagens around Compound A5.

Figure 8:
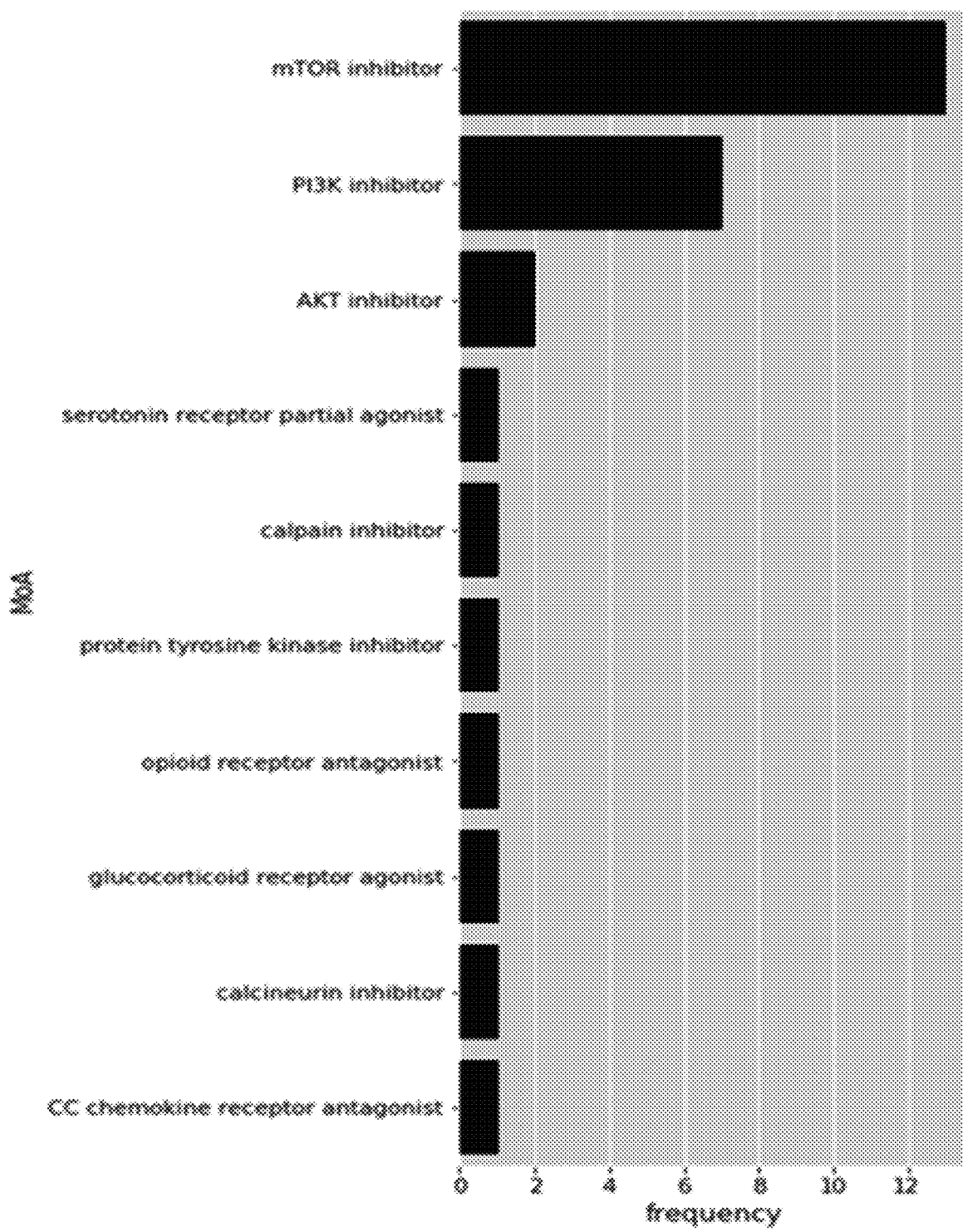
FIG. 8 illustrates characterizations of a compound cluster formed around Compound A5, an mTOR and PI3K inhibitor. Specifically.

Annotated mechanisms of action (MoA) for each member of the Compound A5 cluster were evaluated. As illustrated in FIG. 8, the cluster is enriched for both mTOR inhibitors and PI3K inhibitors. Further, the cluster is also enriched with structural analogs for Compound A5, despite that the analysis did not use any structural information for selection. The structural analogs were sufficient to permit pharmacophore modeling and should facilitate de novo molecular design.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer readable storage medium. For instance, the computer program product could contain the program modules shown in any combination of FIG. 1 or 2. These program modules can be stored on a CD-ROM, DVD, magnetic disk storage product, or any other non-transitory computer readable data or program storage product.

Plural instances may be provided for components, operations or structures described herein as a single instance. Finally, boundaries between various components, operations, and data stores are somewhat arbitrary, and particular operations are illustrated in the context of specific illustrative configurations. Other forms of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first dataset could be termed a second dataset, and, similarly, a second dataset could be termed a first dataset, without departing from the scope of the present invention. The first dataset and the second dataset are both datasets, but they are not the same dataset, unless otherwise specified.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of screening a plurality of compounds comprising at least 50 compounds, wherein each compound in the plurality of compounds is associated with a corresponding plurality of exposure conditions, the method using a plurality of cells lines that comprises 5 or more cell lines and a plurality of biomarkers that comprises 25 or more different biomarkers, the method comprising:
   (A) for each combination of (i) a compound in the plurality of compounds and (ii) an exposure condition in the corresponding plurality of exposure conditions associated with the compound:
       (a) exposing an aliquot of each cell line in the plurality of cell lines to the compound in the plurality of compounds under the exposure condition in the corresponding plurality of exposure conditions associated with the compound, and
       (b) obtaining a response signature for each aliquot of each cell line in the plurality of cell lines, that comprises a plurality of quantitative biomarker measurements of the aliquot of the cell line, the plurality of quantitative biomarker measurements including a separate quantitative biomarker measurement for each biomarker in the plurality of biomarkers, upon exposure of the aliquot of the cell line to the compound in the plurality of compounds under the exposure condition in the corresponding plurality of exposure conditions associated with the compound,
   thereby obtaining a plurality of response signatures, wherein
       the plurality of response signatures includes a response signature for each aliquot of each cell line in the plurality of cell lines for each combination of (i) a compound in the plurality of compounds and (ii) an exposure condition in the corresponding plurality of exposure conditions associated with the compound,
       each corresponding plurality of exposure conditions for each compound in the plurality of compounds comprises at least five exposure conditions for the compound, and
       each exposure condition in the corresponding plurality of exposure conditions for a compound comprises a combination of a duration of exposure and a concentration of the compound for exposure;
   at a computer system comprising a memory and one or more processors:
   (B) determining, for each combination of (i) a first compound in the plurality of compounds and an exposure condition in the corresponding plurality of exposure conditions associated with the first compound and (ii) a second compound in the plurality of compounds and an exposure condition in the corresponding plurality of exposure conditions associated with the second compound:
       a correlation value, for each cell line in the plurality of cell lines that comprises at least five cell lines, that is a correlation of (1) quantitative biomarker measurements for the plurality of at least 25 biomarkers of the cell line in a response signature in the plurality of response signatures that represents the cell line upon exposing an aliquot of the cell line to the first compound at the exposure condition in the corresponding plurality of exposure conditions associated with the first compound and (2) quantitative biomarker measurements for the plurality of the at least 25 biomarkers of the cell line in the response signature in the plurality of response signatures that represents the cell line upon exposing an aliquot of the cell line to the second compound at the exposure condition in the corresponding plurality of exposure conditions associated with the second compound,
   thereby determining a corresponding plurality of correlation values for each pair of first and second compounds in the plurality of compounds for each cell line in the plurality of cell lines;
   (C) determining a plurality of weight sets for each pair of first and second compounds in the plurality of compounds, for each cell line in the plurality of cell lines, wherein each weight set is a summary statistic of a subset of the corresponding plurality of correlation values for the pair of first and second compounds across each exposure condition in the plurality of exposure conditions associated with the first or second compound;

(D) forming a plurality of sparse weight sets by removing from each weight set in the plurality of weight sets those weights that fail to satisfy a threshold value;
(E) determining a single comparison score for each pair of first and second compounds in the plurality of compounds using the plurality of sparse weights sets associated with the first and second compounds, thereby determining a plurality of comparison scores;
(F) forming a compound cluster, for a first compound in the plurality of compounds, wherein the compound cluster consists of each compound in the plurality of compounds that shares a single comparison score in the plurality of comparison score with the first compound that exceeds a threshold value
(G) determining that a test compound is in the compound cluster that contains the first compound, wherein the first compound is associated with a disease; and
(H) responsive to determining that the test compound is in the compound cluster, associating the test compound with the disease
wherein the plurality of biomarkers is any combination of nucleic acids, ribonucleic acids, carbohydrates, lipids, epigenetic features, metabolites, and proteins.

2. The method of claim 1, wherein the threshold value is between five percent and fifty percent.

3. The method of claim 1, wherein the threshold value is five percent.

4. The method of claim 1, wherein the threshold value is ten percent.

5. The method of claim 1, wherein the threshold value is fifteen percent.

6. The method of claim 1, wherein each plurality of quantitative biomarker measurements in each response signature is normalized against a response signature of one or more control genes in the respective cell line.

7. The method of claim 1, wherein the plurality of cell lines comprises 10 or more different cell lines.

8. The method of claim 1, wherein the plurality of compounds is between 100 compounds and $1 \times 10^7$ compounds.

9. The method of claim 1, wherein, for a pair of first and second compounds in the plurality of compounds, the summary statistic of the subset of the corresponding plurality of correlation values is a measure of central tendency of the subset of the corresponding plurality of correlation values.

10. The method of claim 1, wherein the correlation value for a cell line in the plurality of cell lines that is correlation of (1) quantitative biomarker measurements for the plurality of at least 25 biomarkers of the cell line in the response signature in the plurality of response signatures that represents the cell line upon exposing an aliquot of the cell line to the first compound at the exposure condition in the corresponding plurality of exposure conditions associated with the first compound and (2) quantitative biomarker measurements for the plurality of at least 25 biomarkers of the cell line in the response signature in the plurality of response signatures that represents the cell line upon exposing an aliquot of the cell line to the second compound at the exposure condition in the corresponding plurality of exposure conditions associated with the second compound is a Pearson correlation value.

11. The method of claim 1, wherein
the compound cluster contains the test compound, and the method further comprises:
associating the test compound as being a drug for a second disease indication on the basis that one or more properties of one or more compounds, in the compound cluster that contains the test compound is associated with the second disease condition, thereby repurposing the drug for the second disease indication.

12. The method of claim 1, the method further comprising performing pharmacophore analysis of one or more compounds in the compound cluster.

13. The method of claim 1, wherein the method further comprises determining that the test compound and the first compound share a common mechanism-of-action annotation responsive to the determining that the test compound is in the compound cluster.

14. The method of claim 1, wherein each quantitative biomarker measurement in the plurality of quantitative biomarker measurements is a colorimetric measurement.

15. The method of claim 1, wherein each quantitative biomarker measurement in the plurality of quantitative biomarker measurements is a resonance energy transfer (FRET) measurement.

16. The method of claim 1, wherein a Tanimoto coefficient between a fingerprint of the test compound and a fingerprint of the first compound is less than 0.80.

17. The method of claim 1, wherein a Tanimoto coefficient between a fingerprint of the test compound and a fingerprint of the first compound is less than 0.60.

18. The method of claim 16, wherein the fingerprint is a Daylight fingerprint, a BCI fingerprint, an ECFP4 fingerprint, an EcFC fingerprint, an MDL fingerprint, an atom pair fingerprint (APFP fingerprint), a topological torsion fingerprint (TTFP), a UNITY 2D fingerprint, an RNNS2S fingerprint, or a GraphConv fingerprint.

19. The method of claim 1, wherein a cell line in the plurality of cell lines is drawn from cells of an organ.

20. The method of claim 1, wherein a cell line in the plurality of cell lines is drawn from cells of a tissue.

21. The method of claim 1, wherein a cell line in the plurality of cell lines is drawn from:
a plurality of stem cells,
a plurality of primary human cells,
umbilical cord blood,
peripheral blood,
bone marrow, or
solid tissue.

22. The method of claim 1, wherein the plurality of compounds comprises at least 2500 compounds and the plurality of biomarkers comprises 150 or more biomarkers.

23. The method of claim 1, wherein the plurality of biomarkers is nucleic acids.

24. The method of claim 1, wherein the disease is hyperparathyroidism, metabolic bone disease, chronic kidney failure, asthma, or chronic obstructive pulmonary disease.

25. The method of claim 1, wherein each quantitative biomarker measurement in the plurality of quantitative biomarker measurements is a fluorescence measurement.

26. The method of claim 1, wherein each quantitative biomarker measurement in the plurality of quantitative biomarker measurements is a luminescence measurement.

27. The method of claim 1, wherein the plurality of biomarkers is nucleic acids.

28. The method of claim 1, wherein the plurality of biomarkers is ribonucleic acids.

29. The method of claim 1, wherein the plurality of biomarkers is proteins.

* * * * *